US006855707B2

(12) United States Patent
Cincotta

(10) Patent No.: US 6,855,707 B2
(45) Date of Patent: Feb. 15, 2005

(54) METHOD FOR THE TREATMENT OF LIPID AND GLUCOSE METABOLISM DISORDERS

(75) Inventor: Anthony H. Cincotta, Charlestown, MA (US)

(73) Assignee: Pliva D.D., Zagreb (HR)

( * ) Notice: Subject to any disclaimer, the term of this patent is extended or adjusted under 35 U.S.C. 154(b) by 0 days.

(21) Appl. No.: 09/950,167

(22) Filed: Sep. 10, 2001

(65) Prior Publication Data

US 2002/0187985 A1 Dec. 12, 2002

Related U.S. Application Data

(63) Continuation of application No. 08/848,538, filed on Apr. 28, 1997, now abandoned.
(60) Provisional application No. 60/017,377, filed on May 7, 1996, and provisional application No. 60/019,336, filed on Jun. 6, 1996.

(51) Int. Cl.[7] .................... A61K 31/4985; A61K 31/48; A61K 31/55
(52) U.S. Cl. .................................. 514/213.01; 514/250
(58) Field of Search ........................... 514/250, 213.01, 514/213, 284, 288

(56) References Cited

U.S. PATENT DOCUMENTS

| | | | | |
|---|---|---|---|---|
| 3,074,847 A | 1/1963 | Bigsby et al. | ............... | 514/271 |
| 3,752,814 A | 8/1973 | Fluckiger et al. | ............ | 544/346 |
| 3,752,888 A | 8/1973 | Fluckiger et al. | ........... | 514/250 |
| 3,922,347 A | 11/1975 | Bach et al. | ................... | 514/288 |
| 4,054,660 A | 10/1977 | Clemens et al. | ............ | 514/288 |
| 4,239,763 A | 12/1980 | Milavec et al. | ............. | 514/250 |
| 4,659,715 A | 4/1987 | Meier et al. | ................. | 514/288 |
| 4,749,709 A | 6/1988 | Meier et al. | ................. | 514/288 |
| 4,783,469 A | 11/1988 | Meier et al. | ................. | 514/288 |
| 5,006,526 A | 4/1991 | Meier et al. | ................. | 514/250 |
| 5,468,755 A | 11/1995 | Cincotta et al. | ............ | 514/866 |

FOREIGN PATENT DOCUMENTS

| | | |
|---|---|---|
| BE | 890369 | 3/1982 |
| GB | 2192541 A | 1/1988 |
| JP | 57-8231 | 9/1980 |

OTHER PUBLICATIONS

Jackson et al., Journal of Neural Transmission, 69(1–2) 131–45 (1987) (abstract).*
Kotani et al., Japanese J. Pharmacology, 54, (1990),482–486.*
Barnett, Post Graduate Medical J., 56:11–14 (1980).
Bartness et al., J. Exp. Zoology, 244:437–454 (1987).
Berle, Acta endocr., Suppl. 173, Abstract No. 104 (1973).
Brus, et al., "Modulation of Glucose Uptake in Rat Brain After Administration of Quinpirole and SKF–38393, Two Central Dopamine–Receptor Agonists", Pharmacology Communications, 7:87–91 (1995).

Burns et al., Int'l. Symp. on Chronopharm and Chronother (1988).
Cassar, J. et al. "Bromocriptine Treatment of Acromegaly," Metabolism, 26: 539–546 (1977).
Chemical Abstracts, 109:66888W (1988).
Chemical Abstracts, 112:75773U (1990).
Cincotta et al., J. Endocrinol, 106:177–181 (1985).
Cincotta et al., J. Endocrinol, 106:173–176 (1985).
Cincotta et al., Life Sciences, 45:2247–2254 (1989).
Cincotta, J. Endocrinol, 103:141–146 (1984).
Cincotta et al., J. Endocrinol, 120:385–391 (1989).
Cincotta et al. Ann Nutr Metab, 33:305–314 (1989).
Cincotta et al., Experientia, 43:416–417 (1987).
Cincotta et al., Horm Metabol Res, 21:64–68 (1989).
De Mattia et al., La Clinica Terapeutica, vol. XI (1983).
Dolocek, R. et al. "Bromocriptine and glucose tolerance in acromegalics," Pharmatherapeutica 3:100–106 (1982).
Eisemann et al., J. of Animal Sci, 59:95–104 (1984).
Eisemann et al., J. of Animal Sci, 59:86–94 (1984).
Emata et al., J. Exp. Zoology, 233:29–34 (1985).
Eskildsen, P.C. et al., "Long–Term Treatment of Acromegaly with Bromocriptine", Acta Endocr. 87: 687–700 (1978).
Goldstein, M., EMBASE Abstract No. 90266123, Psychopharmacol. Bull, 25/3:349–352 (1989).
Harel et al., Proc. La. Acad. Sci., 38:125 (1975).
Horseman et al., General and Comparative Endocrinology, 38:269–274 (1979).
Horseman et al., J. Endocr, 82:367–372 (1979).
Joseph et al., J. Exp. Zool, 178:59–62 (1971).
Joseph et al., Proc. Soc. Exp. Bio. Med., 146:1150–1155 (1974).
Komorowski et al., Aliment. Nutr. Metab, 1:293 (1980).
Landgraf et al., Deutschen Gessellschaft fur innere Medizin (Apr. 25–25, 1976).
Larson et al., Lakartidningen, 82:4425 (1985).
Lee et al., J. Exp. Zool, 166:307–316 (1967).
Lobato et al. Mol. and Cell. Biochem, 67:19–23 (1985).
Martin et al., The Condor, 75: 369–374 (1973).
Martin et al., Neuroendocrinology, 52: 9–14 (1990).
Martin et al., Chronobiology, 641–646 (1974).
Martin et al., Proc. La. Acad. Sci., 38:127 (1975).
Martin et al., Ame Zoologist, 18:572 (1978).
Martin, Dissertation LSU (1974).

(List continued on next page.)

Primary Examiner—Phyllis Spivack
(74) Attorney, Agent, or Firm—Darby & Darby

(57) ABSTRACT

Disclosed are methods for modifying or regulating at least one of glucose or lipid metabolism disorders which comprises administering to a human or vertebrate subject a $D_1$ dopamine agonist in conjunction with a dopamine $D_2$ agonist where the conjoined administration is effective to improve at least one of the following lipid and glucose metabolic indices: body weight, body fat, plasma insulin, plasma glucose and plasma lipid, and plasma lipoprotein. In preferred embodiments, the administration of the $D_1$ dopamine agonist and the $D_2$ dopamine agonist is conducted at a predetermined time.

14 Claims, 18 Drawing Sheets

OTHER PUBLICATIONS

Martin, Thesis, Sam Houston State College (1969).
Meier, *Amer. Scientist,* 61:184–187 (1973).
Meier et al., *Biology of Reproduction,* 8:400–410 (1973).
Meier et al., *General and Comparative Endocrinology,* 26:253–258 (1975).
Meier et al., *General and Comparative Endocrinology,* 3:499–508 (1972).
Meier et al., *Proc. Soc. Exp. Biol. and Med.,* 133:1113–16 (1970).
Meier et al., *Science,* 173:1240–42 (1971).
Meier et al., *Gen. & Comp. Endocrin,* 17:311–318 (1971).
Meier et al., *Proc. Soc. for Exp. Bio. & Med,* 137:408–415 (1971).
Meier et al., *Gen. & Comp. Endocrin,* 8:110–114 (1967).
Meier et al., *Transactions of the American Fisheries Society,* 113:422–431 (1984).
Meier et al., *Current Ornithology,* 2:303–343 (1984).
Meier et al., Circadian hormone basis for seasonal conditions in the gulf killifish *"Fundus grandi",* In *Comparative Endocrinology,* pp. 141–144. Galliard et al. (eds), Elsevier/North Holland Biomedical Press, Amsterdam (1978).
Meier et al., *Amer. Zool,* 16:649–659 (1976).
Meier et al., *Amer. J. of Physiology,* 232:E193–E196 (1977).
Meier et al., *Experientia,* 48:248–253 (1992).
Meier et al., *Physiol. Zool,* 41:95–103 (1968).
Miller et al., *J. Interdiscipl. Cycle Res.,* 14:75–84 (1983).
Miller et al., *J. Interdiscipl. Cycle Res.,* 14:85–94 (1982).
Moore et al., *Biology of Reproduction,* 36:47–58 (1987).
Ottenweller et al., *Life Sciences,* 28:1033–1040 (1981).
Spieler et al., *Life Sciences,* 22:255–258 (1977).
Southern et al., *J. Animal Sci.,* 68:931–936 (1990).
Steinbeck, K. and J.R Turtle, "Treatment of Acromegalywith Bromocryptine," *Aust. N.Z. J. Med.* 9: 217–224 (1979).
Thomas et al., *Sem. des Hosp. de Paris,* 53(34–35):1857–1862 (1977).
Tozzo, et al, "Diabetes", 45(Suppl. 2):105A (1996).
Wass, J.A.H. et al. "An Assessment of Glucose Intolerance In Acromegaly and Its Response to Medical Treatment," *Clin. Endocr.,* 12: 53–59 (1980).
Wilson, *Chrono. Bio. Int.* 6:113–121 (1989).
Phillips et al., *Psychopharmacology,* 117:82–90 (1995).
Saller et al., *Brain Research,* 546:235–250 (1991).
Bordi et al., *Faseb Journal,* vol. 3 (1989).
Laudrelle et al., *Fundamental & Clinical Pharmacology,* 5:481–490 (1991).
Terry et al., *Obesity Research,* 3:515S–523S (1995).
Zarrindast et al., *General Pharmacology,* 22:1011–1016 (1991).
Samanin et al., *Therapie,* 51:107–115 (1996).
Samanin et al., *Pharmacology & Toxicology,* 73:63–68 (1993).
Wellman, *American Journal of Clinical Nutrition,* 55:193S–198S, (1992).

* cited by examiner

Control 1.17±0.05 µg lipid/cell

BC+SKF 0.74±0.03 µg lipid/cell

METHOD FOR THE TREATMENT OF LIPID AND GLUCOSE METABOLISM DISORDERS

This is a continuation of application Ser. No. 08/848,538 filed Apr. 28, 1997, now abandoned. The prior application is hereby incorporated herein by reference, in its entirety. This application claims priority under 35 U.S.C. §119 from provisional applications Ser. Nos. 60/017,377, filed May 7, 1996 and 60/019,336, filed Jun. 6, 1996 the disclosures of which are incorporated herein in their entirety.

FIELD OF THE INVENTION

This invention relates to novel, improved methods for modifying or regulating in a subject (vertebrate animal or human) of at least one of lipid and glucose metabolism.

BACKGROUND OF THE INVENTION

Obesity and Lipid Metabolism Disorders—Body Fat Loss

In humans obesity can be defined as a body weight exceeding 20% of the desirable body weight for individuals of the same sex, height and frame (Salans, L. B., in *Endocrinology & Metabolism*, 2d Ed., McGraw-Hill, N.Y. 1987, pp. 1203–1244; see also, R. H. Williams, *Textbook of Endocrinology*, 1974, pp. 904–916). In other animals (or also in humans) obesity can be determined by body weight patterns correlated with prolactin profiles given that members of a species that are young, lean and "healthy"(i.e., free of any disorders, not just metabolic disorders) have daily plasma prolactin level profiles that follow a pattern characteristic of the species. This pattern is highly reproducible with a small standard deviation. Members of a species suffering from at least one of lipid and metabolism disorders, however, have aberrant prolactin profiles that depart from the normal (or healthy subjects') pattern by at least 1 SEM in at least two spaced apart time points or by at least 2 SEM (standard error of the mean) in at least one time point.

Obesity, or excess fat deposits, correlate with and may trigger the onset of various lipid and/or glucose metabolism disorders, e.g. hypertension, Type II diabetes, atherosclerosis, etc.

Even in the absence of clinical obesity (according to the above definition) the reduction of body fat stores (notably visceral fat stores) in man especially on a long-term or permanent basis would be of significant benefit, both cosmetically and physiologically.

The reduction of body fat stores in domestic animals (as well as pets) especially on a long-term or permanent basis would also obviously be of considerable economic benefit to man, particularly since farm animals supply a major portion of man's diet; and the animal fat may end up as de novo fat deposits in man.

Whereas controlled diet and exercise can produce modest results in the reduction of body fat deposits, prior to the cumulative work of the present inventors (including the prior co-pending patent applications and issued U.S. patents referred to below), no truly effective or practical treatment had been found for controlling obesity or other lipid metabolism disorders.

Hyperlipoproteinemia is a condition in which the concentration of one or more of cholesterol- or triglyceride-carrying lipoproteins (such as chylomicrons, very low density lipoproteins or VLDL and low-density lipoproteins or LDL) in plasma exceeds a normal limit. This upper limit is generally defined as the ninety-fifth percentile of a random population. Elevated levels of these substances have also been positively correlated with atherosclerosis and the often resulting cardiac infarction, or "heart attack", which accounts for approximately half of all deaths in the United States. Strong clinical evidence has been presented which correlates a reduction in plasma lipoprotein concentration with a reduced risk of atherosclerosis (Noma, A., et al, *Atherosclerosis* 49:1, 1983; Illingworth, D. and Conner, W., in *Endocrinology & Metabolism*, McGraw-Hill, N.Y. 1987). Thus, a significant amount of re-search has been devoted to finding treatment methods which reduce levels of plasma cholesterol and triglycerides. High LDL and/or VLDL accompanied by high triglyceride levels in the blood constitute most important risk factors for atherosclerosis. Reduction of one or both of lipoproteins and triglycerides in the blood would reduce the risk of atherosclerosis and arrest or retard its development.

Another subset of the plasma lipoproteins found in vertebrates are high density lipoproteins, or HDL. HDL serve to remove free cholesterol from the plasma. A high HDL concentration as a percentage of total plasma cholesterol has been associated with a reduced risk of atherosclerosis and heart disease. Thus HDL are known in the lay press as "good" cholesterol. Therefore, therapeutic strategies involve attempts both to reduce plasma LDL and VLDL content (that is, reduce total plasma cholesterol), and to increase the HDL fraction of total plasma cholesterol. Several lines of research indicate that simply increasing HDL is of benefit even in the absence of LDL or VLDL reduction: Bell, G. P. et al., *Atherosclerosis* 36:47–54, 1980; Fears, R., *Biochem. Pharmacol.* 33:219–228, 1984; Thompson, G., *Br. Heart J.* 51:585–588, 1989; Blackburn, H. *N.E.J.M.* 309:426–428, 1983.

Current therapies for hyperlipoproteinemias include a low fat diet and elimination of aggravating factors such as sedentary lifestyle. If the hyperlipoproteinemia is secondary (i.e. incident to e.g. a deficiency of lipoprotein lipase or LDL receptor, various endocrine pathologies, alcoholism, renal disorders, hepatic disorders) then control of the underlying disease is also central to treatment. Hyperlipoproteinemias are also treated with drugs, which usually alter the levels of particular components of the total plasma cholesterol, as well as reduce the total plasma lipid component. Among the most recently introduced drugs to treat hyperlipoproteinemia is lovastatin (MEVACOR®) which selectively inhibits an enzyme involved in cholesterol production, 3-hydroxy-3-methylglutaryl coenzyme A (HMG-CoA) reductase. This drug specifically reduces total cholesterol and can cause a modest (5–10%) increase in HDL concentrations. However, benefits from these therapies vary from subject to subject.

Moreover, use of the HMG-CoA enzyme inhibitor is sometimes accompanied by side effects such as liver toxicity, renal myoglobinuria, renal shutdown, and lenticular opacity. The risk of such side effects necessitates close monitoring of the patients (e.g., liver function is tested monthly).

Another drug prescribed against hyperlipoproteinemia is clofibrate. The effectiveness of clofibrate also varies from subject to subject and its use is often accompanied by such side effects as nephrotic syndromes, myalgia, nausea and abdominal pain.

Diabetes and Glucose Metabolism Disorders

Diabetes, one of the most insidious of the major diseases, can strike suddenly or lie undiagnosed for years while attacking the blood vessels and nerves. Diabetics, as a group, are far more often afflicted with blindness, heart disease, stroke, kidney disease, hearing loss, gangrene and impotence. One third of all visits to physicians are occasioned by this disease and its complications, and diabetes and its complications are a leading cause of untimely death in the United States and in the Western world.

Diabetes adversely affects the way the body uses sugars and starches which, during digestion, are converted into glucose. Insulin, a hormone produced by the pancreas, makes the glucose available to the body's cells for energy. In muscle, adipose (fat) and connective tissues, insulin facilitates the entry of glucose into the cells by an action on the cell membranes. The ingested glucose is normally converted in the liver to $CO_2$ and $H_2O$ (50%); to glycogen (5%); and to fat (30–40%), the latter being stored in fat depots. Fatty acids from the adipose tissues are circulated, returned to the liver for re-synthesis of triacylglycerol and metabolized to ketone bodies for utilization by the tissues. The fatty acids are also metabolized by other organs. Fat formation is a major pathway for carbohydrate utilization.

The net effect of insulin is to promote the storage and use of carbohydrates, protein and fat. Insulin deficiency is a common and serious pathologic condition in man. In insulin-dependent (IDDM or Type I) diabetes the pancreas produces little or no insulin, and insulin must be injected daily for the survival of the diabetic. In noninsulin-dependent (NIDDM or Type II) diabetes the pancreas retains the ability to produce insulin and in fact may produce higher than normal amounts of insulin, but the amount of insulin is relatively insufficient, or less than fully effective, due to cellular resistance to insulin.

In either form of diabetes there are widespread abnormalities. In most NIDDM subjects, the fundamental defects to which the abnormalities can be traced are (1) a reduced entry of glucose into various "peripheral" tissues and (2) an increased liberation of glucose into the circulation from the liver. There is therefore an extracellular glucose excess and an intracellular glucose deficiency. There is also a decrease in the entry of amino acids into muscle and an increase in lipolysis. Hyperlipoproteinemia is also a complication of diabetes. The cumulative effect of these diabetes-associated abnormalities is severe blood vessel and nerve damage.

Other than the present invention and previous work by the present inventors (discussed below), no effective treatment has been found for controlling either hyperinsulinemia or insulin resistance. Hyperinsulinemia is a higher-than-normal level of insulin in the blood. Insulin resistance can be defined as a state in which a normal amount of insulin produces a subnormal biologic response. In insulin-treated patients with diabetes, insulin resistance is considered to be present whenever the therapeutic dose of insulin exceeds the secretory rate of insulin in normal persons. Insulin resistance is also associated with higher-than-normal levels of insulin i.e. hyperinsulinemia—when normal or elevated levels of blood glucose are present.

Previous Work in this Field

Studies by the present inventors and others have indicated that the naturally occurring annual cycle of body fat store level, pervasive among vertebrates in the wild, reflects the activities of an adjustable central metabolistat that is comprised of circadian hypothalamic neural components. Changes in the phase-relationships of circadian dopaminergic and serotonergic activities induce seasonal changes in metabolism and these circadian activities can be adjusted by appropriately timed treatments with hormones or neurotransmitter affecting drugs. In this regard, bromocriptine, a sympatholytic dopamine $D_2$ agonist with $\alpha_2$ agonistic and $\alpha_1$ antagonistic activities as well as serotonin inhibiting activities has been demonstrated to reduce body fat store levels in a variety of animals including humans, without reducing food consumption, and also to reduce hyperinsulinemia, hyperlipidemia, and glucose intolerance.

The present inventors and their co-workers have previously found that administration of either or both of (i) certain prolactin reducing dopamine ($D_2$) agonists such as bromocriptine and (ii) prolactin-increasing substances such as dopamine antagonists, such as metoclopramide; and serotonin agonists and precursors, such as 5-hydroxytryptophan, reduce body fat stores, obesity, plasma triglycerides and cholesterol as well as hyperglycemia, hyperinsulinemia and insulin resistance: U.S. Pat. Nos. 4,659,715; 4,749,709; 4,783,469; 5,006,526.

It is preferred to administer the prolactin reducing substances at a first predetermined time to effect a decrease in the circulating prolactin levels of the subject to be treated during an interval within the subject's daily prolactin cycle or rhythm when circulating (blood) prolactin levels are low in young, healthy subjects of the same species thereby causing the prolactin rhythm of the treated to approach or to conform to the standard or healthy subjects' prolactin rhythm. It is also preferred to administer the prolactin-increasing substances at a second predetermined time to effect an increase in the circulating prolactin levels of the subject to be treated during an interval within the subject's daily prolactin cycle or rhythm when circulating (blood) prolactin levels are high in young healthy subjects of the same species, thereby causing the prolactin rhythm of the treated subject to approach, or conform to, the standard or healthy subjects' prolactin rhythm. U.S. Pat. Nos. 5,468,755; 5,496,803; 5,344,832, U.S. Pat. No. 5,585,347 and U.S. patent application Ser. No. 08/456,952 and PCT applications US93/12701 and US95/09061.

It is also known in the art that some of the effects of bromocriptine are supported by endogenous dopamine. (*Ergot Compounds and Brain Functions Neuropsychiatric Aspects: Advances in Biochemical Psychopharmacology.* M. Goldstein et al, Eds. (Raven Press, New York, 1980) vol. 23). Specifically, it has been shown that locomotor stimulation and stereotyped behavior responses to bromocriptine are blocked by depletion of endogenous dopamine in rodents. However, if a $D_1$ agonist is subsequently provided to dopamine depleted animals, the responsiveness to bromocriptine is restored. Jackson, D. M. et al, *Psychopharmacology* 94:321 (1988)). A similar dopaminergic $D_2:D_1$ interaction has been demonstrated in dopaminergic inhibition of feeding behavior. Although these studies confirm the importance of a $D_2:D_1$ interaction in the activation of dopaminergic activities, the increased locomotor activity and decreased feeding response to $D_2:D_1$ agonists is acute and short lived, lasting for only a few hours. (Cooper, S. J. et al., in $D_1:D_2$ *Dopamine Receptor Interactions*, J. Waddington, Ed. (Academic Press, London, 1993) pp. 203–234).

The previous work by third parties with $D_1$ and $D_2$ dopamine agonists in combination has not demonstrated any effects on lipid and glucose metabolism, and has not produced long-term responses of dopaminergic activities. Significantly, the present inventors have now found that the conjoined administration of a $D_1$ agonist and a $D_2$ dopamine agonist (or at least one of an adrenergic $\alpha_1$ antagonist, an adrenergic $\alpha_2$ agonist and a serotonergic inhibitor) result in an unexpected and surprising improvement in one or more of the metabolic indices related to lipid and glucose metabolism when compared to the improvement (if any) provided by administration of a dopamine $D_2$ agonist such as bromocriptine administered alone.

OBJECTS OF THE INVENTION

It is one of the objects of this invention to provide additional improved methods for reducing in vertebrate subjects (including humans) in need of such treatment at least one of food consumption, body weight, body fat, plasma or blood glucose and blood insulin.

Another object of this invention is to provide methods for reducing at least one of insulin resistance (impaired glucose tolerance), hyperinsulinemia and hyperglycemia, and glycosylated hemoglobin (including A1C), and abating Type II diabetes.

A further object is to provide methods for reducing or retarding or arresting atherosclerosis by reducing at least one of hyperlipoproteinemia and elevated blood triglycerides.

It is another object of this invention to provide methods for modifying and regulating lipid and glucose metabolism in a manner beneficial to the subject.

It is still another object of the invention to provide methods for modifying and regulating lipid and glucose metabolism to provide effective treatments for obesity.

SUMMARY OF THE INVENTION

It has now been found that at least one of the foregoing objects can be accomplished by administering to a subject in need of such treatment a dopamine $D_1$ agonist in conjunction with one agent or agent combination selected from the following:

(i) a dopamine $D_2$ agonist;

(ii) at least one of an adrenergic $\alpha_1$ antagonist, an adrenergic $\alpha_2$ agonist and a serotonergic inhibitor;

(iii) a dopamine $D_2$ agonist further conjoined with at least one of an adrenergic $\alpha_1$ antagonist, an adrenergic $\alpha_2$ agonist and a serotonergic inhibitor.

Preferably, the foregoing agents in (i), (ii) or (iii) above ("conjoined agents") are administered at a predetermined time i.e. within a restricted portion of a 24-hour period. Since the dopamine $D_1$ agonist amplifies the effect of the other agent or agents, the $D_1$ agonist is also preferably administered at about the same time.

The conjoined administration of a dopamine $D_1$ agonist with one (or more) of the other agents identified above results in substantially augmented, and in fact often synergistic, effects in improvement of one or more metabolic indices related to glucose or lipid metabolism, and thus an improved modification or regulation of at least one of glucose and lipid metabolism.

Where a $D_2$ agonist is employed, it is preferably an ergot alkaloid, most preferably bromocriptine.

In another aspect, the present invention is directed to administering to said subject:

(i) a $D_2$ agonist; and (ii) at least one agent, not a $D_2$ agonist, selected from the group consisting of adrenergic $\alpha_1$ antagonists, adrenergic $\alpha_2$ agonists and serotonergic inhibitors.

It has been found that such conjoined administration effects a greater improvement on one or more of the foregoing metabolic indices than administration of a $D_2$ agonist singly.

DETAILED DESCRIPTION OF THE INVENTION

Figure 1:
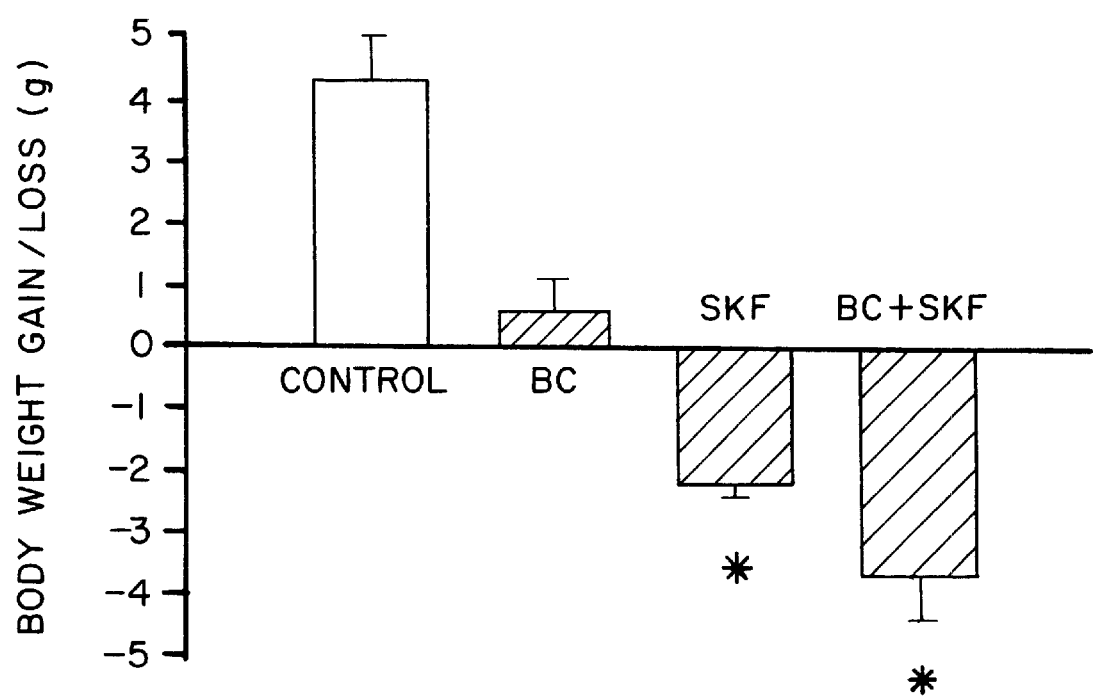
FIG. 1 is a bar graph illustrating the weight loss (negative bars) or gain (positive bars) obtained in the experimental group administered both bromocriptine (BC) and SKF 38393 (SKF) compared to the animals administered SKF alone or BC alone or nothing (negative controls).

All literature and patents and patent applications cited herein are incorporated by reference in their entirety. In case of a conflict, the present disclosure including its definitions shall control.

In one embodiment of the method of the present invention, a $D_1$ dopamine agonist is administered in conjunction with a second agent, consisting of at least one of a $D_2$ agonist, an $\alpha_2$ agonist, an $\alpha_1$ antagonist and a serotonergic inhibitor (or a $D_2$ agonist and at least one of the remaining agents) preferably at a specific time of day to a subject in need of treatment.

As used herein and applied to administration of more than one active ingredient the terms "conjoined" or "in conjunction" mean that the subject being thus treated receives a first active agent and also at least one other active agent, but not necessarily within the same formulation or dosage form and not necessarily at the same administration time. For example, the $D_1$ agonist and $D_2$ agonist or the other agent(s) can be administered at the same time (in the same dosage form or in two or more divided dosage forms) or sequentially at different times and in different dosage forms.

The $D_1$ dopamine agonist may be any one or more of those substances known to those skilled in the art that are capable of activating or potentiating D1 dopamine receptors. The $D_1$ agonists that are suitable for use in the present invention include SKF38393, dihydrexidine, SKF 75670, SKF 82957, A77636, A68930, and SKF 82526 (fenoldopam).

The $D_2$ agonists for use in the present invention can be any one or more of those compounds known to those skilled in the art that are capable of activating $D_2$ dopamine receptors. $D_2$ agonists suitable for use in the present invention include LY-171555, bromocriptine methane sulfonate (+)-, 2,10,11-trihydroxyaporphine HBr, R(—)—, fisuride hydrogen maleate, 2-OH-NPA HCl, R(—)—, MDO-NPA HCl R(—), Propylnorpamorphine HCl R(—)—(NPA), and Quinperole HCl.

A preferred class of $D_2$ agonists includes ergot alkaloids such as 2-bromo-α-ergocriptine (bromocriptine), 6-methyl 8 β-carbobenzyloxy-aminoethyl-10-α-ergoline, 8-acylaminoergoline, 6-methyl-8-α-(N-acyl)amino-9-ergoline, pergolide, lisuride, 6-methyl-8-α-(N-phenyl-acety) amino-9-ergoline, ergocornine, 9,10-dihydroergocornine, any D-2-halo-6-alkyl-8-substituted ergoline, and D-2-bromo-6-methyl-8-cyanomethylergoline. Of these bromocriptine is most preferred.

Effective amounts of ergot alkaloid for humans and vertebrates when administered alone (not conjoined to a $D_1$ agonist) are typically within the range of 5.0 ug/kg/day to 0.2 mg/kg/day.

In general, effective amounts of $D_2$ agonist for humans and vertebrates are within the range of 5 ug/kg/day to 3.5 mg/kg/day.

The $\alpha_1$ antagonists for use in the present invention can be any one or more of those compounds known to those skilled in the art that directly or indirectly block activation of $\alpha_1$ adrenoceptors. The $\alpha_1$ antagonists suitable for use in the present invention include bromocriptine, benoxathin HCl, naftopidil 2HCl, (±)-niguldipine HCl, S(+)-niguldipine HCl, prazosin HCl, doxazosin HCl, spiperone HCl, urapidil HCl, 5-methyl urapidil, WB-4101 HCl.

Effective amounts of $\alpha_1$ antagonist for humans and vertebrates are generally within the range of 0.02 to 0.3 mg/kg/day.

The $\alpha_2$ agonists for use in the present invention can be any one or more of those compounds known to those skilled in the art that are capable of activating $\alpha_2$ adrenoceptors. The $\alpha_2$ agonists suitable for use in the present invention include bromocriptine, agmatine sulfate, p-aminoclonidine HCl, B-HT 920 diHCl, B-HT 933 diHCl, clonodine HCl, guanabenz acetate, p-iodoclonidine HCl, oxymetazoline HCl, UK 14,304, and xylazine HCl.

Effective amounts of $\alpha_2$ agonist for humans and vertebrates are generally within the range of 1 ug/kg/day to 0.3 mg/kg/day.

The serotonergic inhibitors suitable for use in the present invention include bromocriptine.

Effective amounts of serotonergic inhibitors for humans and vertebrates are generally within the range of 5 ug/kg/day to 0.2 mg/kg/day.

When two (or more) agents are administered in conjunction as disclosed in the Summary of Invention the amount of one or another can be lower than stated above, and even amounts that are subthreshold (when an agent is used singly) can be employed.

The dopamine $D_1$ agonist and the dopamine $D_2$ agonist and/or other agent conjoined with the $D_1$ agonist (or with the $D_2$ agonist) may be administered to a subject preferably orally, or by subcutaneous, intravenous or intramuscular injection. Dermal delivery systems, e.g., skin patches, as well as suppositories and other well-known systems for administering pharmaceutical agents can also be employed. Sublingual, nasal and other transmucosal modes of administration are also contemplated. Accelerated release compositions, such as those disclosed in U.S. patent application Ser. No. 08/459,021, are preferred.

Each of the $D_2$ agonist, $\alpha_1$ antagonist, $\alpha_2$ agonist and serotonergic inhibitor are preferably administered at a predetermined time. The reason is that the effect of each of these agents on lipid and/or glucose metabolism is time-sensitive, as is explained in more detail for $D_2$ agonists in in U.S. Pat. No. 5,585,347 and U.S. patent application Ser. No. 08/456,952, but applicable to the $\alpha_1$ antagonists, $\alpha_2$ agonists and serotonergic inhibitors. The preferred time of administration is within an interval that results in effective blood levels of the agent(s) at a time during which the standard prolactin levels in healthy subjects of the species to be treated are low. For example in humans standard prolactin levels are low between the hours of 9:00 and 22:00. Accordingly, the predetermined time of administration of one or more of the foregoing agents is between the hours of 5:00 and 13:00, preferably 7:00 and 12:00. Divided doses can be administered and the schedule of administration can be varied to take into account pharmocokinetic properties of each active agent. Details of administration are given in U.S. Pat. No. 5,585,347 and U.S. patent application Ser. No. 08/456,952 for bromocriptine, but also apply to the $\alpha_1$ antagonists, $\alpha_2$ agonists and serotonergic inhibitors employed in the present invention.

For mice the preferred time of administration of the active agent is within 1 hour after light onset. It is further preferred that the administration take place when the subject is neither active nor feeding.

For other vertebrate animals the preferred time of administration can be ascertained by reference to the standard prolactin rhythm for the species of the animal to be treated. The standard prolactin curve can be generated by measuring prolactin in young, healthy members of the species over a 24 hour period. See in U.S. Pat. No. 5,585,347 and U.S. patent application Ser. No. 08/456,952.

The administration of the $D_1$ agonist is also preferably timed, i.e. the $D_1$ agonist is also administered at a predetermined time. Because the $D_1$ agonist amplifies the effect of the conjoined agent, it is advantageous to administer the $D_1$ agonist at or about the time of administration of the conjoined agent(s), such that the activity period of the $D_1$ agonist in the bloodstream of the treated subject overlaps (in fact preferably overlaps as much as possible) with the activity period of the conjoined agent. For convenience of administration and in order to promote subject compliance, the $D_1$ agonist can be administered at the same time as the conjoined agent(s).

The $D_1$ agonist may but need not be in the same formulation or dosage form (or form part of the same composition) as the conjoined agent(s). If more than one conjoined agent is administered, the conjoined agents may but need not be in the same formulation or dosage form or form part of the same composition.

In treating vertebrates, generally, dosages of the $D_1$ agonist and conjoined agent(s) are typically administered over a period ranging from about 10 days to about 180 days, or longer. Some patients (e.g., patients in particularly poor physical condition, or those of advanced age) may require a longer, or even continuous treatment. A treatment duration exceeding six months or even continuous treatment may be desirable even when not required.

At least one of body fat deposits, body weight, plasma or blood glucose, circulating insulin, plasma triglycerides (TG), plasma free fatty acids (FFA) and food consumption of the subject will be reduced as the result of the treatment. Disorders of lipid and glucose metabolism are thereby treated and subjects suffering from such pathologies as hyperphagia, obesity, insulin resistance (impaired glucose tolerance), hyperlipidemia, hyperinsulinemia, and hyperglycemia will exhibit improvement in corresponding metabolic indices.

While appropriately timed administration of certain $D_2$ agonists (i.e., bromocriptine) alone will produce the effects described above to some degree, these effects are amplified (potentiated) by the conjoined administration of the $D_1$ agonist agents described in the present invention. In other words, the synergistic effect of the conjoined administration of the $D_1$ agonist and the conjoined agent (i.e., a $D_2$ agonist, and/or $\alpha_1$ antagonist, and/or serotonergic inhibitor and/or $\alpha_2$ agonist) produces results that are superior to those experienced through administration of the same amount of a $D_2$ agonist alone. It should be noted that the present invention permits but does not require each agent to be administered in an amount over the threshold amount (in the absence of a conjoined agent) to improve one or more metabolic indices precisely because of the augmented effect on these indices achieved by conjoined administration according to the present invention.

The benefits of the invention are not limited to modifying and regulating lipid and glucose metabolism. Other bodily functions, such as blood pressure, can be beneficially modified and regulated by timed administration of a $D_2$ agonist (as monotherapy) in the dosage range disclosed above. For example, the $D_2$ agonist bromocriptine administered at a dose within the range disclosed above (4.8 mg/day at 8:00 AM) has been shown by the present inventor to decrease significantly the diastolic blood pressure of humans. Conjoined administration of a dopamine $D_1$ agonist and (i) a dopamine $D_2$ agonist;

(ii) at least one of an adrenergic $\alpha_1$ antagonist, an adrenergic $\alpha 2$ agonist, and a serotonergic inhibitor;

(iii) a dopamine $D_2$ agonist further conjoined with one or more of the members of (ii) above.

These and other features of the invention will be better understood by reference to the experiments described in the examples below.

EXAMPLE 1

Female ob/ob mice (40–70 g bw) were treated for two weeks with either 1) bromocriptine (11 mg/kg) at light onset, 2) SKF38393 (20 mg/kg) at light onset, 3) bromocriptine plus SKF38393 at light onset, or 4) vehicle at light onset.

Bromocriptine or SKF38393 alone produced moderate reductions in hyperphagia, body weight gain, and obesity. However, bromocriptine plus SKF treatment produced significant reductions in hyperphagia (50–60% p<0.01) resulting in dramatic weight loss (21%, p<0.0001, compared to controls).

Body composition analysis of KOH/EtOH treated carcasses revealed no significant decrease of protein mass and a 22% (p<0.05) decrease of adipose mass in bromocriptine plus SKF treated mice relative to controls. Also, bromocriptine plus SKF treatment decreased to a much greater extent than bromocriptine or SKF alone, plasma free fatty acid (FFA) (44%, p<0.001), triglyceride (TG) (50%, p<0.05), and glucose (57%, p<0.01). Insulin levels tended to decrease (by 50%; p<0.09) and total cholesterol remained unchanged by combined drug therapy.

Larger (65–75 g) animals treated with bromocriptine plus SKF38393 demonstrated an even more dramatic loss of body weight relative to controls (10+1 g in 10 days; p<0.01). Arcuate neuropeptide Y (NPY) mRNA levels remain unchanged after bromocriptine plus SKF treatment compared to controls.

C57BL/6J female obese mice of 40–45 g body weight were treated by daily injections (at 1 HALO) of bromocryptine (BC at 10 mg/kg) and/or SKF38393 (SKF at 20 mg/kg). Animals were held on 12-hour daily photoperiods and fed ad libidum. Food consumption was monitored daily and body weights monitored at days 0, 7 and 14 of the treatment.

Animals were sacrificed at 1 and/or 4 hours after light onset ("HALO") (except as described for FIG. 12A) and blood, liver and adipose tissue were collected. The carcasses were digested in ethanolic KOH and analyzed for protein and lipid content. Blood glucose was measured with an Accu-Chek Advantage glucose meter (Boehringer). Serum insulin was measured with a radioimmunoassay kit (Linco Research) using rat insulin standards. Total triglycerides and free fatty acids were measured with kits from Sigma Diagnostics, St. Louis, Mo. and Wako Chemicals respectively.

Enzymatic activity of fatty acid synthase, malic enzyme and glucose-6-phosphate dehydrogenase was measured in isolated cytosolic fraction by spectrophotometric methods. Phosphoenolpyruvate carboxykinase (PEPCK) in liver cytosol was assayed by incorporation of $H^{14}CO3$- into phosphoenolpyruvate. Glucose-6-phosphatase activity was determined spectrophotometrically in isolated liver microsomes.

Adipocytes were isolated from perigonadal fat pads by collagenase digestion and their size was determined by combining microscopes measurement of their diameter and lipid extraction of their lipid content. Glucose transport and glucose metabolism were measured by U-14C-glucose in the absence and presence of insulin and basal lipolysis was assayed by measuring glycerol release using a $^{32}P$-g-ATP. Neuropeptide Y (NPY) mRNA levels were measured in the arcuate nuclei of the mice using in situ hybridization.

Figure 2:
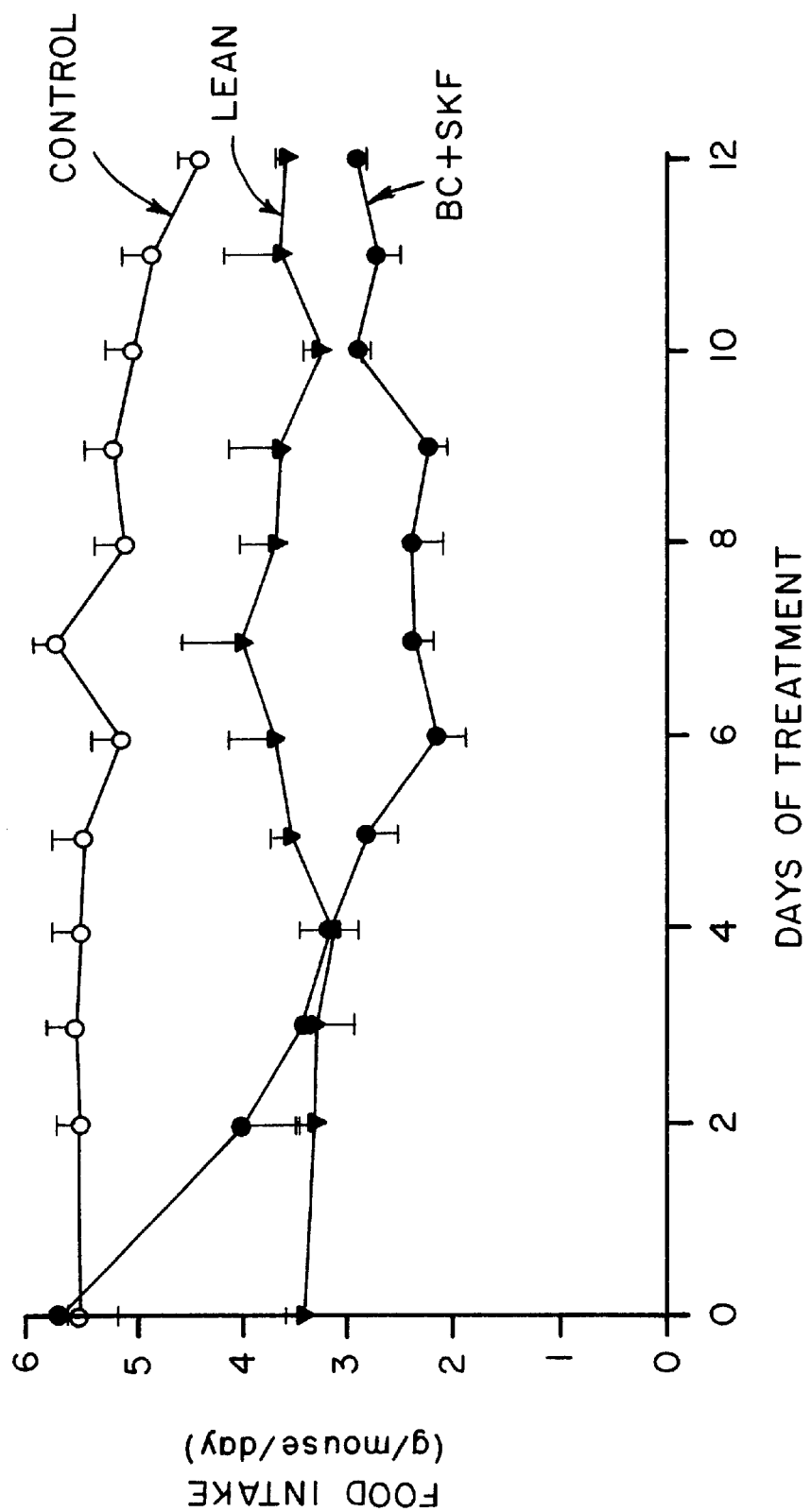
FIG. 2 is a graph of food intake (g/mouse/day) vs days of treatment of experimental ob/ob mice with both bromocriptine and SKF (dark circles) or no drug (open circles) or control lean animals given no drug (dark triangles).

In summary, bromocriptine (BC) plus SKF38393 (SKF) treatment of C57 BL/6 ob/ob mice produces the following changes in metabolic physiology:

(1) A 42% reduction in hyperphagia, reducing daily feeding levels to less than or equal to lean (+/+) controls. (FIG. 2)

(2) A 3.67 g loss of body weight versus a 4.3 g body weight gain in obese controls. (FIG. 1)

Figure 3A:
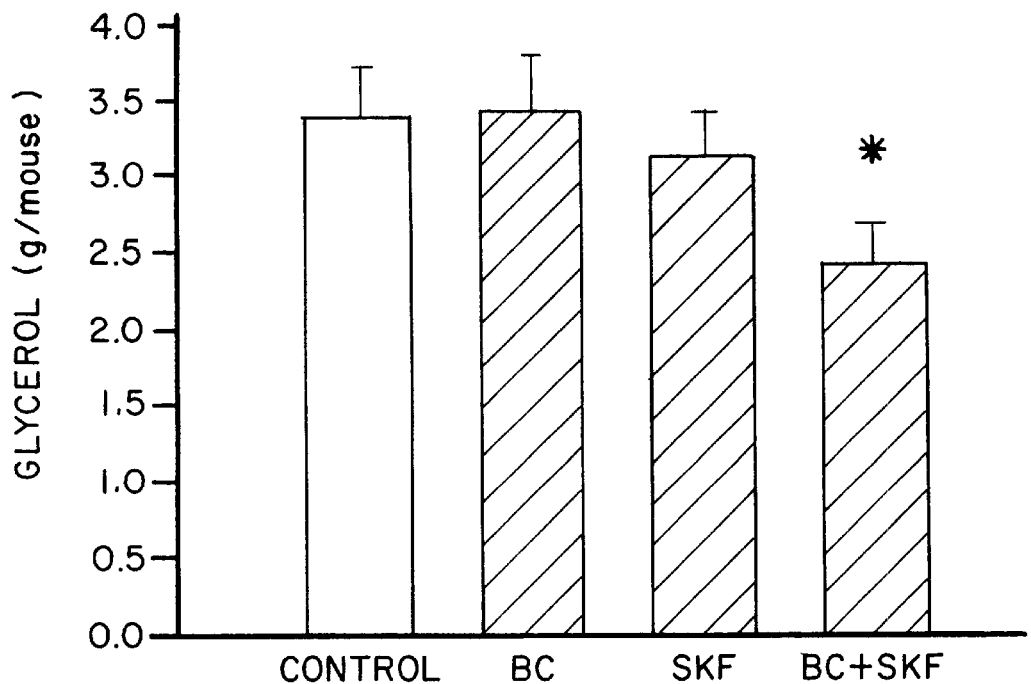
FIGS. 3A and 3B are bar graphs measuring fat body mass measured as glycerol (in g/mouse) (FIG. 3A) or lean body mass (protein in g/mouse) (FIG. 3B) for ob/ob animals that received no drug (control) or bromocriptine alone (second bar from left) or SKF alone (third bar from left) or both BC and SKF (fourth bar). The asterisk indicates a significant difference compared to the control bar.
Figure 3B:
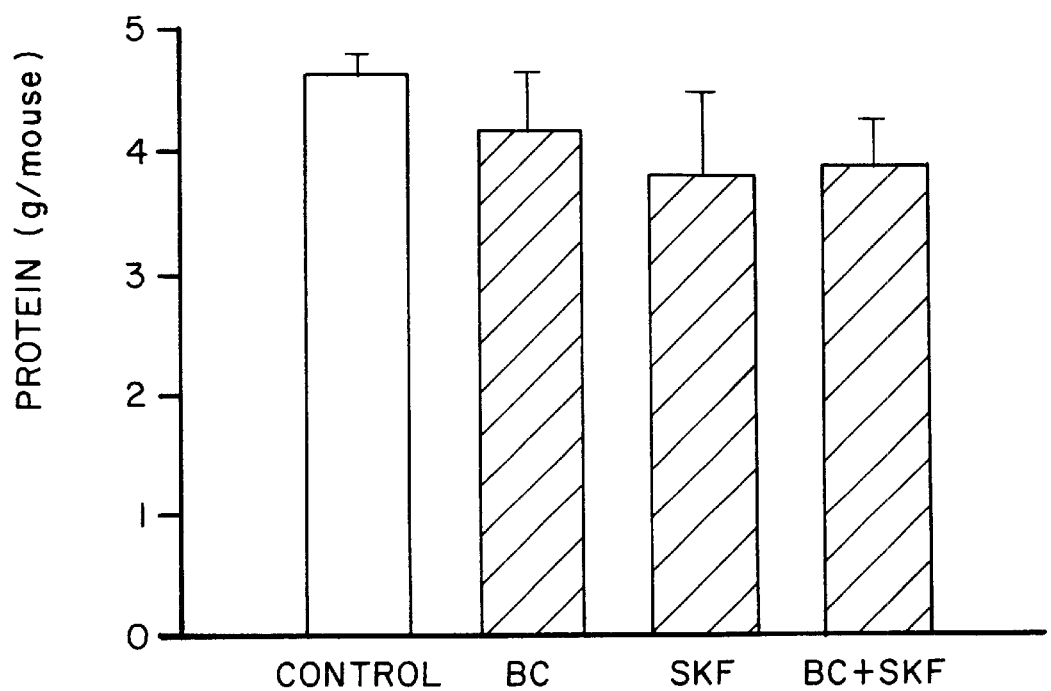

(3) A 27% reduction of body fat mass (FIG. 3A) with no loss of protein (FIG. 3B) despite substantial reduction in food consumption.

Figure 4A:
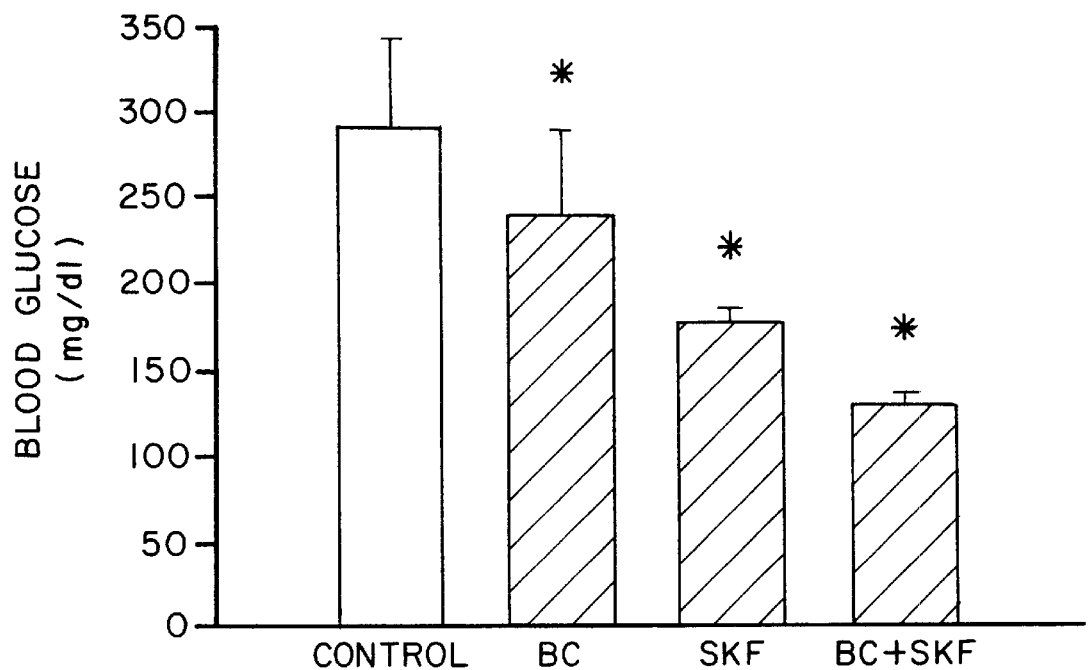
FIGS. 4A and 4B are bar graphs of blood glucose (mg/dl) of ob/ob animals (FIG. 4A) or serum insulin (ng/ml) of ob/ob animals (FIG. 4B) administered no drug (control); left most bar); BC alone (second bar from left); SKF alone (third bar from left) or both BC and SKF (fourth bar). The asterisks have the same significance as for FIG. 3A.
Figure 4B:
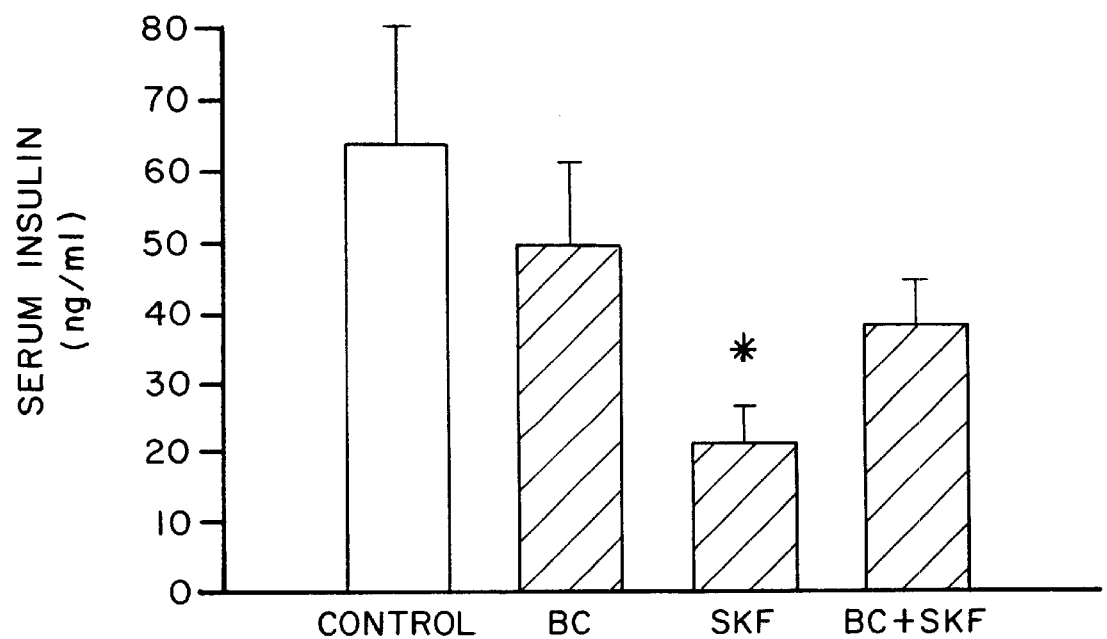

(4) A 57 and 41% reduction in hyperglycemia (FIG. 4A) and hyperinsulinemia (FIG. 4B) respectively.

Figure 5A:
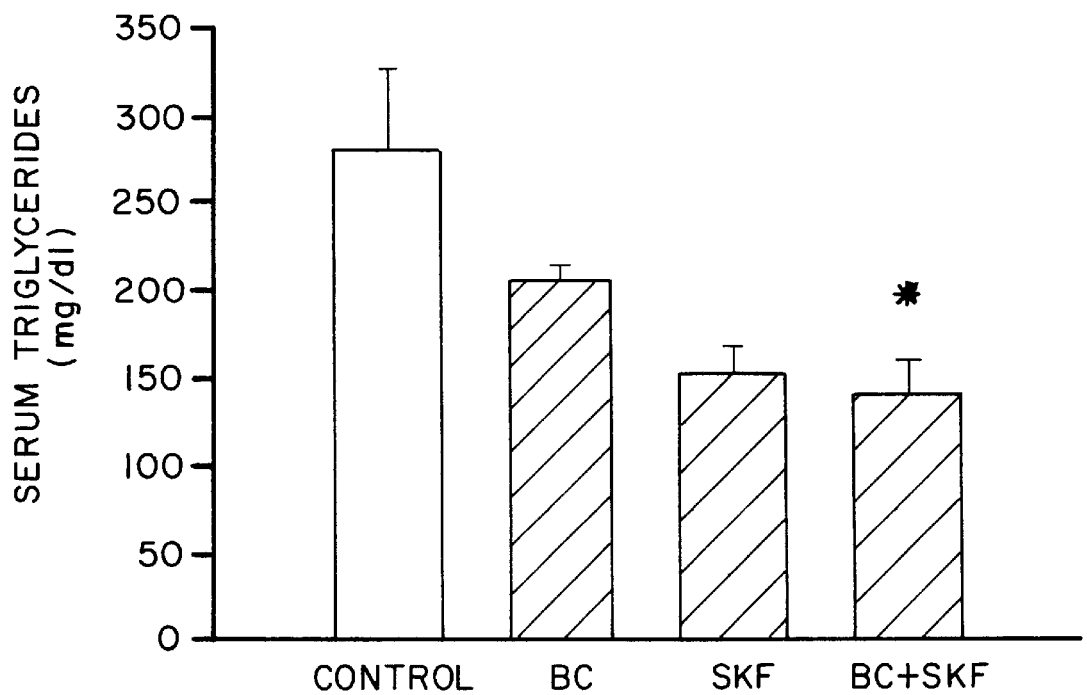
FIGS. 5A and 5B are bar graphs of serum triglyceride levels (TG) in ng/dl (FIG. 5A) or serum free fatty acid levels (FFA) in mmol/l (FIG. 5B) for animals administered no drug (control; left most bar); BC alone (second bar from left); SKF alone (third bar from left) or both BC and SKF (fourth bar). The asterisks have the same significance as for FIG. 3A.
Figure 5B:
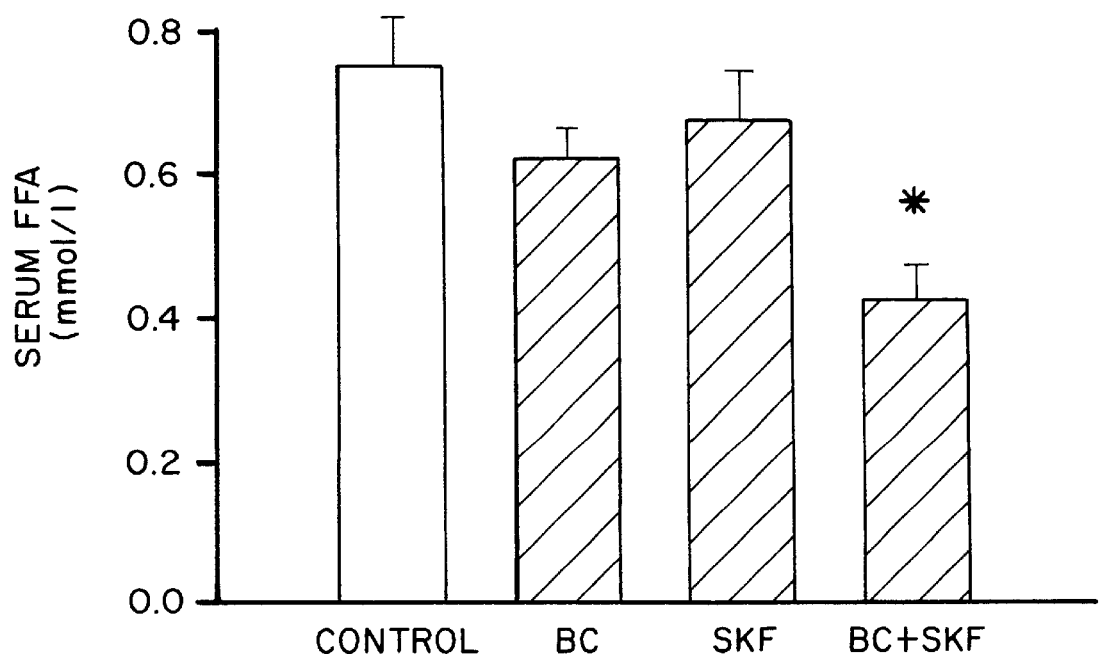

(5) A 44 and 50% reduction serum FFA (FIG. 5B) and TG (FIG. 5A) concentration.

(6) A 27–78% reduction in lipogenesis enzymes within the liver and adipose (FIGS. 7A–7C, 8A–8B, 9A–9C).

Figure 7A:
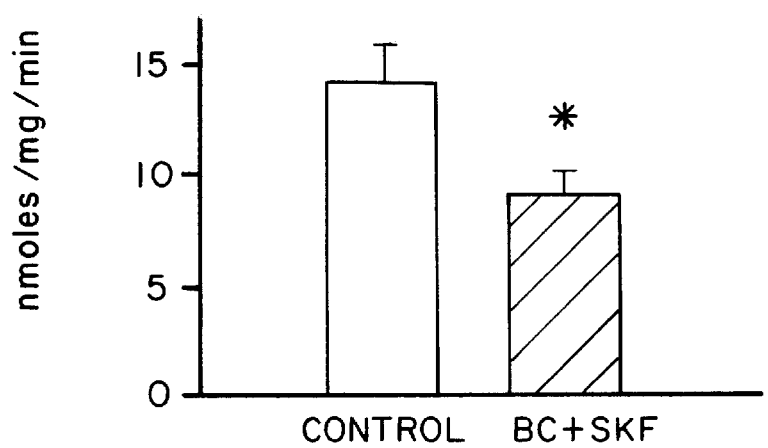
FIGS. 7A–7C are bar graphs of liver enzyme activity (in millimoles of fatty acid per mg protein per minute) for the enzymes involved in fatty acid synthesis in the liver: fatty acid synthetase (FIG. 7A), malic enzyme (FIG. 7B) or glucose-6-phosphatase (FIG. 7C) illustrating difference in said activities as between animals administered no drug (left bar) or both Bc and SKF (right bar). The asterisks have the same significance as for FIG. 3A.
Figure 7B:
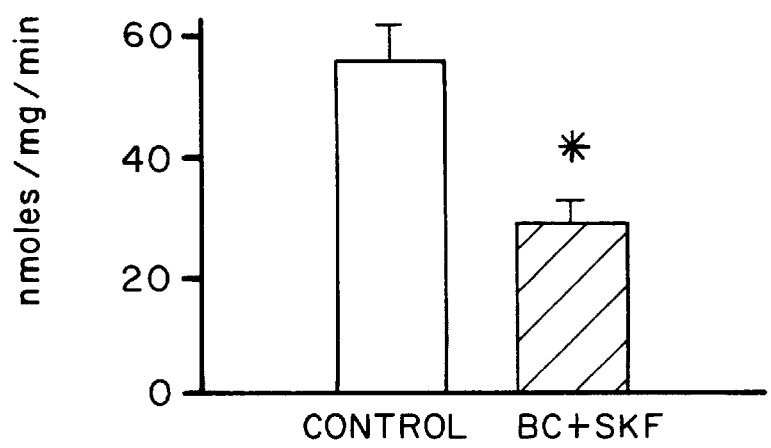
Figure 7C:
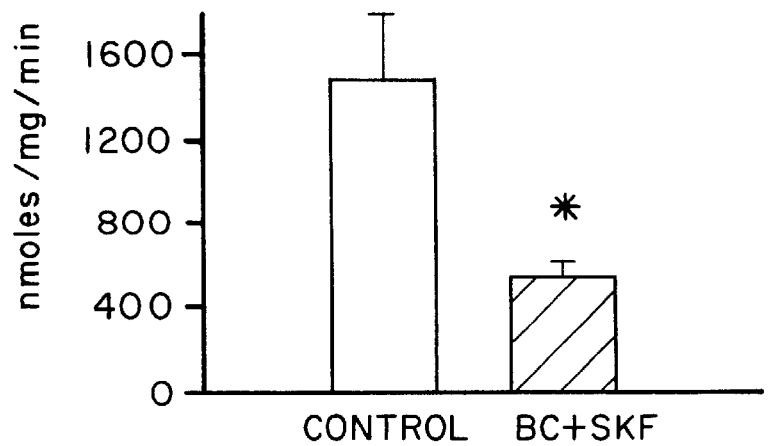
Figure 8A:
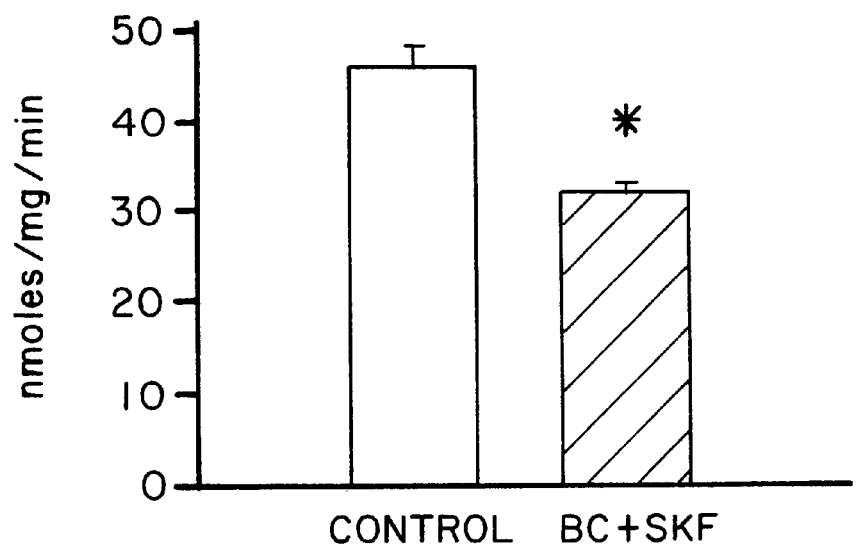
FIGS. 8A and 8B are bar graphs similar to those of FIGS. 7A–7C but for the liver enzymes PEPCK (phosphoenol pyruvate carboxykinase) and glucose-6-phosphate dehydrogenase.
Figure 8B:
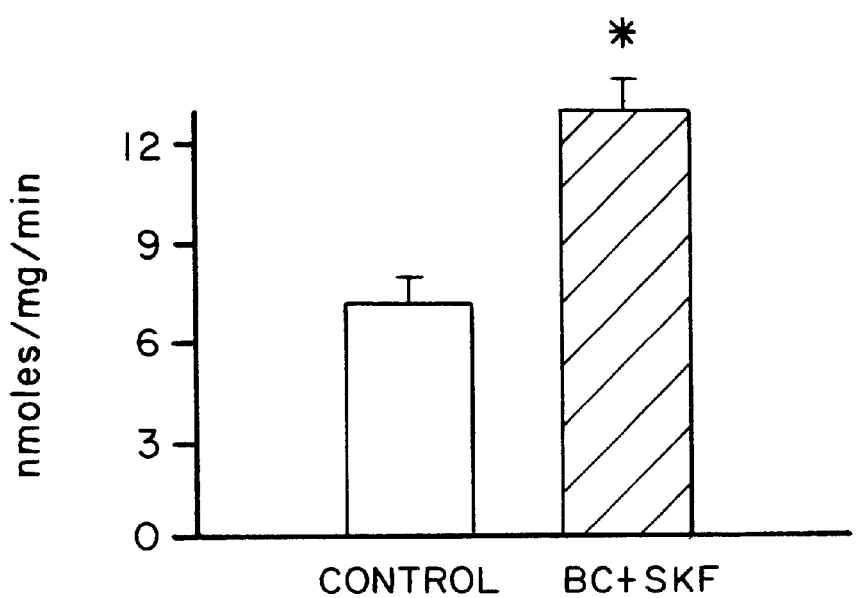
Figure 9A:
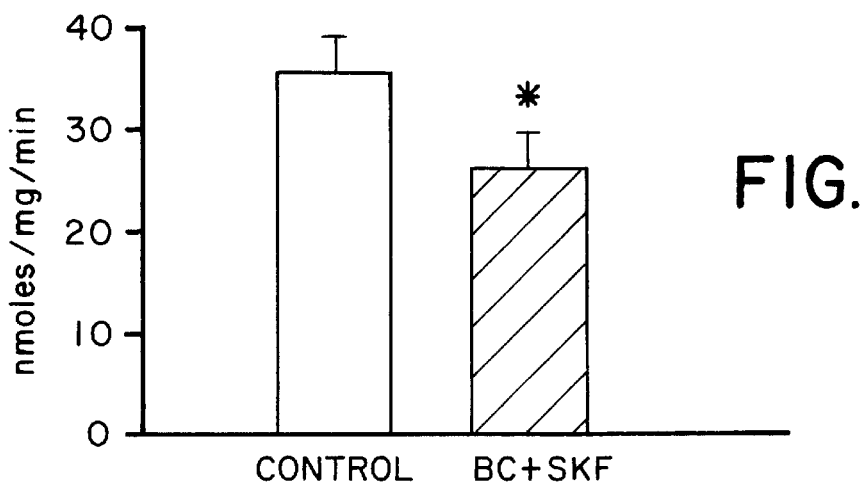
FIGS. 9A–9C are bar graphs similar to hose of FIGS. 7A–7C but for the enzymes involved in fatty acid synthesis in adipose tissue: fatty acid synthetase (FIG. 9A) malic enzyme (FIG. 9B) and glucose-6-phosphate dehydrogenase (FIG. 9C).
Figure 9B:
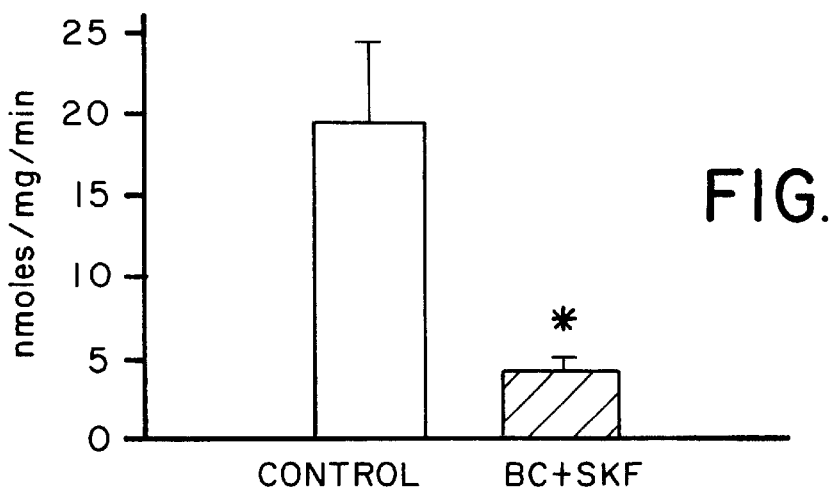
Figure 9C:
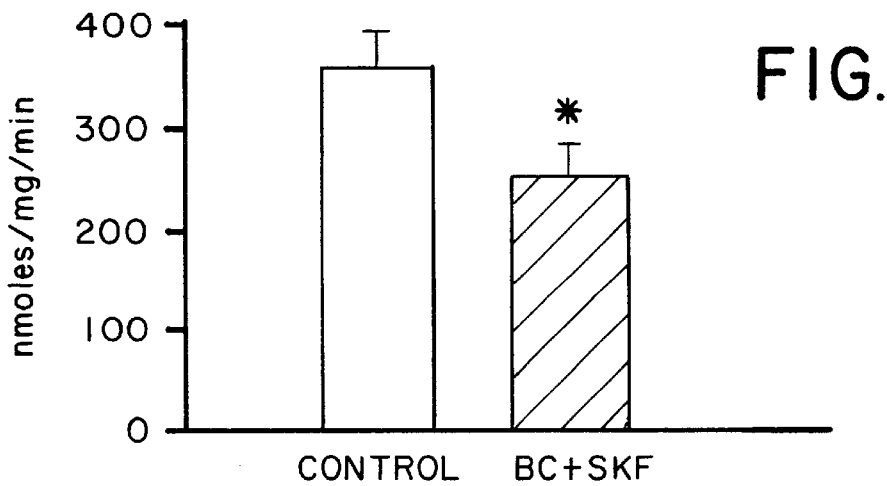

(7) A 64% reduction in liver glucose-6-phosphatase and 80% increase in liver G6P dehydrogenase activities (FIG. 8B) as well as significant reduction in fatty acid synthetase (FIG. 7A) and malic enzyme (FIG. 7B).

Figure 10A:
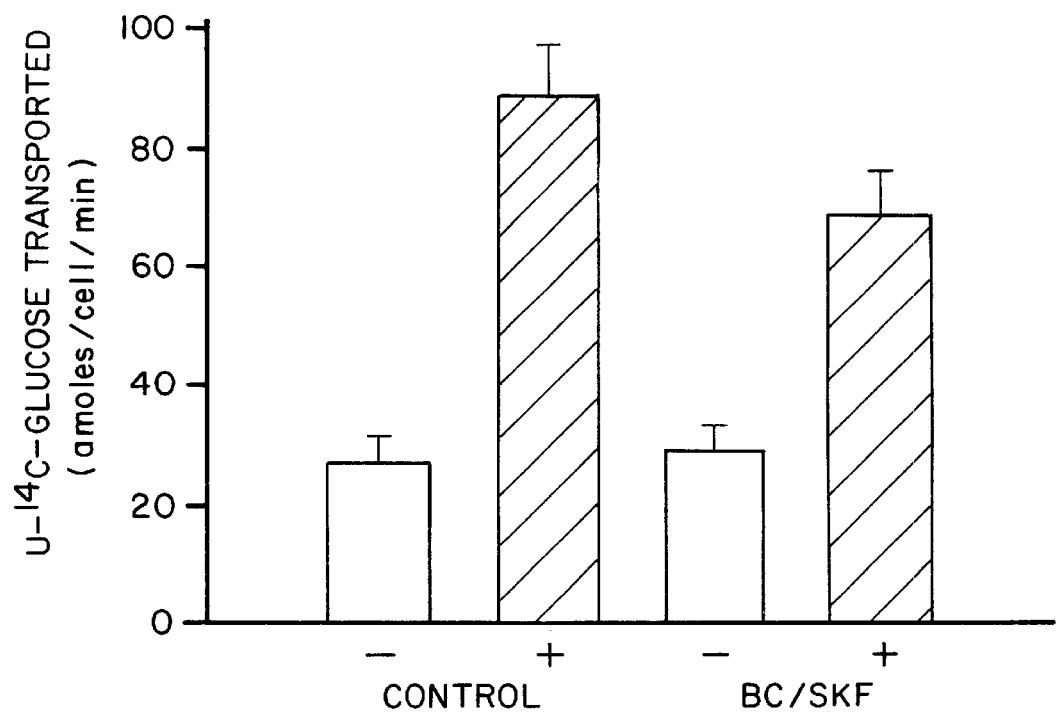
FIGS. 10A and 10B are bar graphs of glucose transport (in amoles/cell/minute) (FIG. 10A) and glucose oxidation in $CO_2$ (in amoles/cell/minute) (FIG. 10B) measured for BC+SKF treated and "no drug" mice in the absence (white bars) and presence (dark bars) of insulin in isolated adipocytes.
Figure 10B:
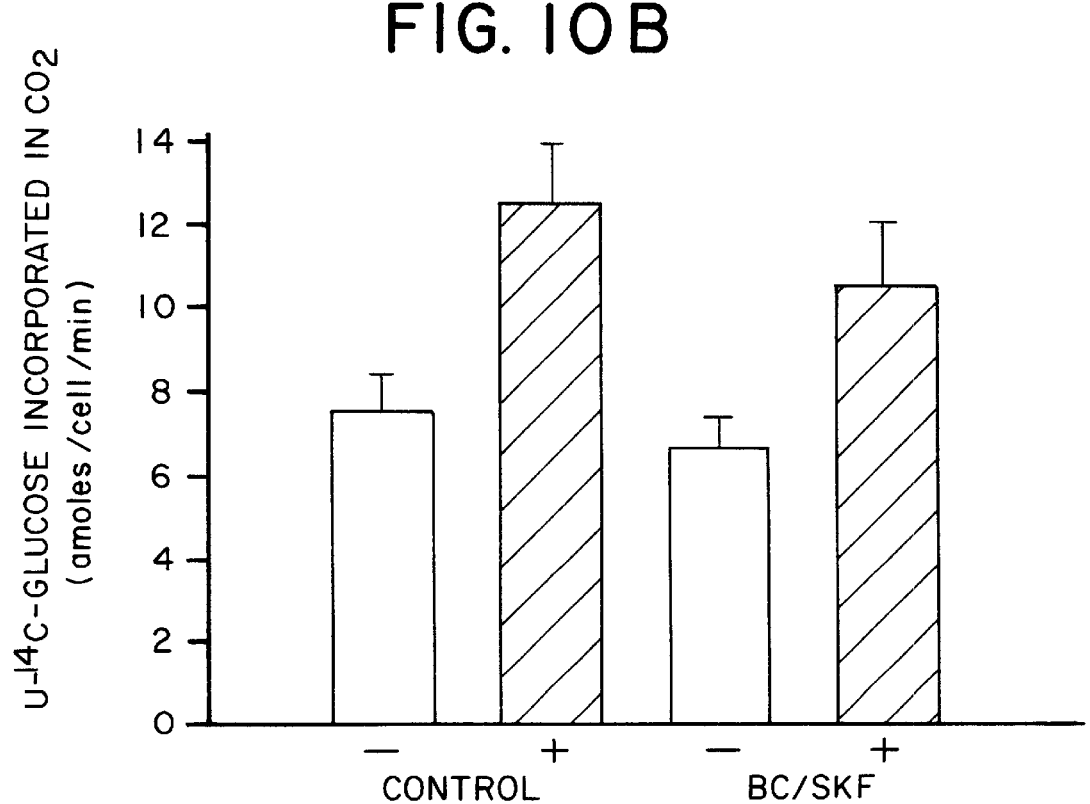
Figure 11:
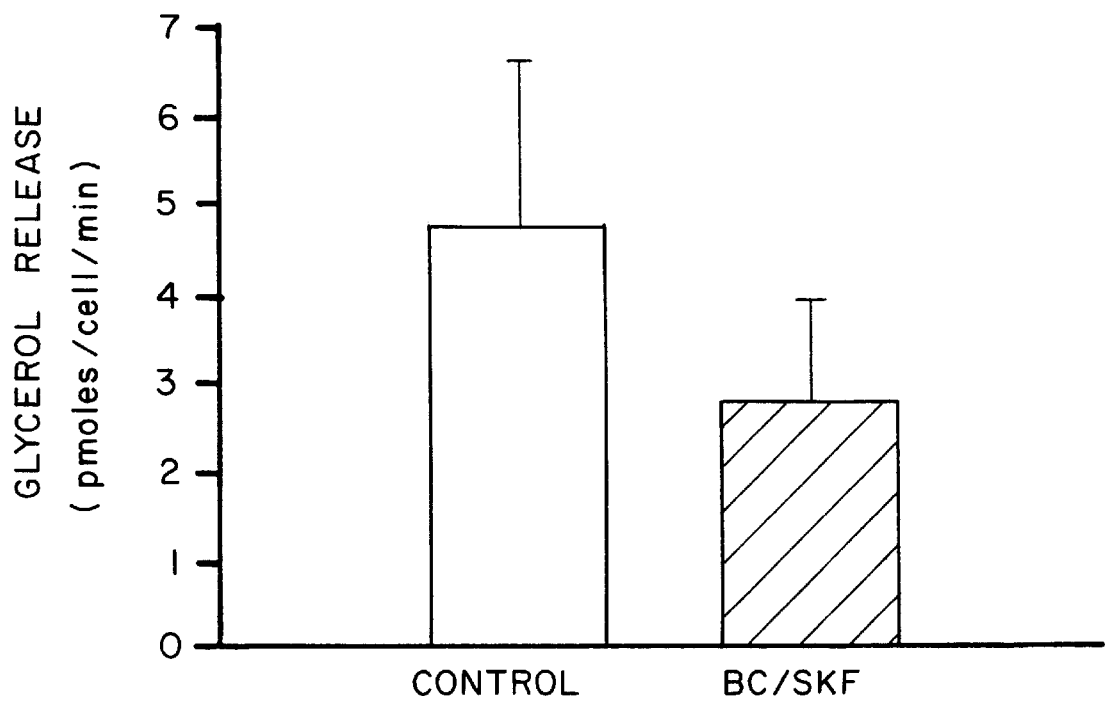
FIG. 11 is a bar graph of lipolysis measured as glycerol release (pmoles/cell/minute) in isolated adipocytes for BC+SKF treated and "no drug" mice.
Figure 13A:
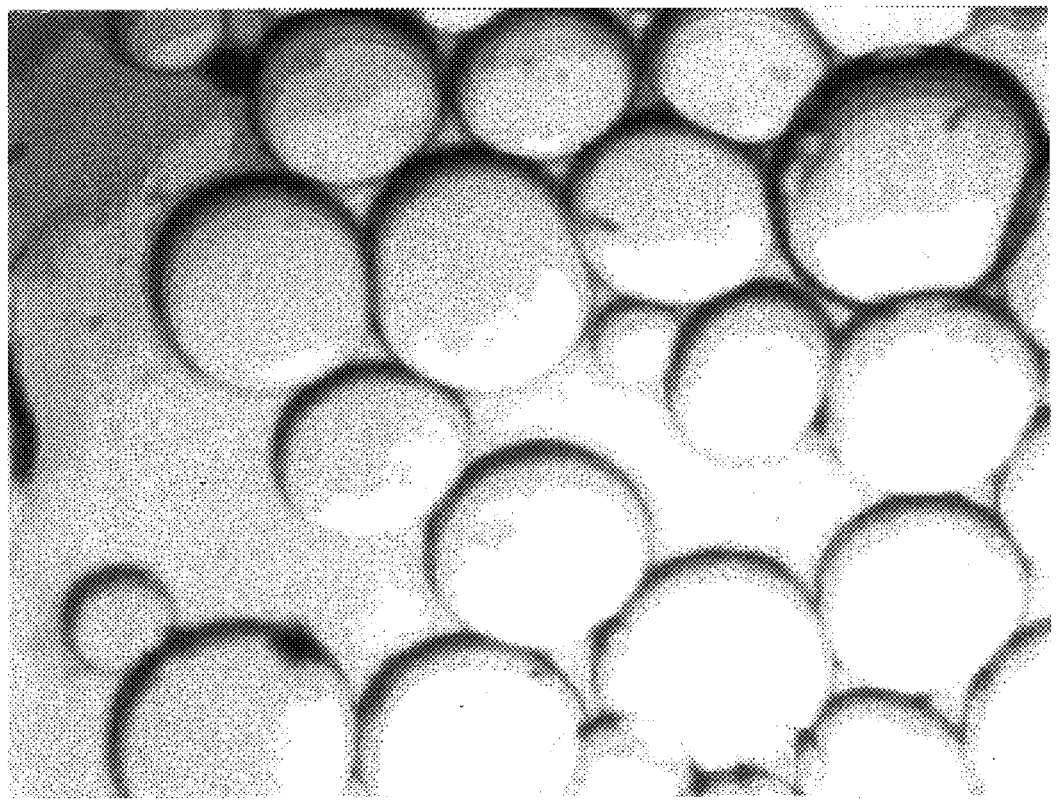
FIGS. 13A and 13B are photomicrographs of adipocytes from BC+SKF treated (FIG. 13B) and untreated (FIG. 13A) animals. The amount of lipid per cell (in μg lipid/cell) are given next to each Figure.
Figure 13B:
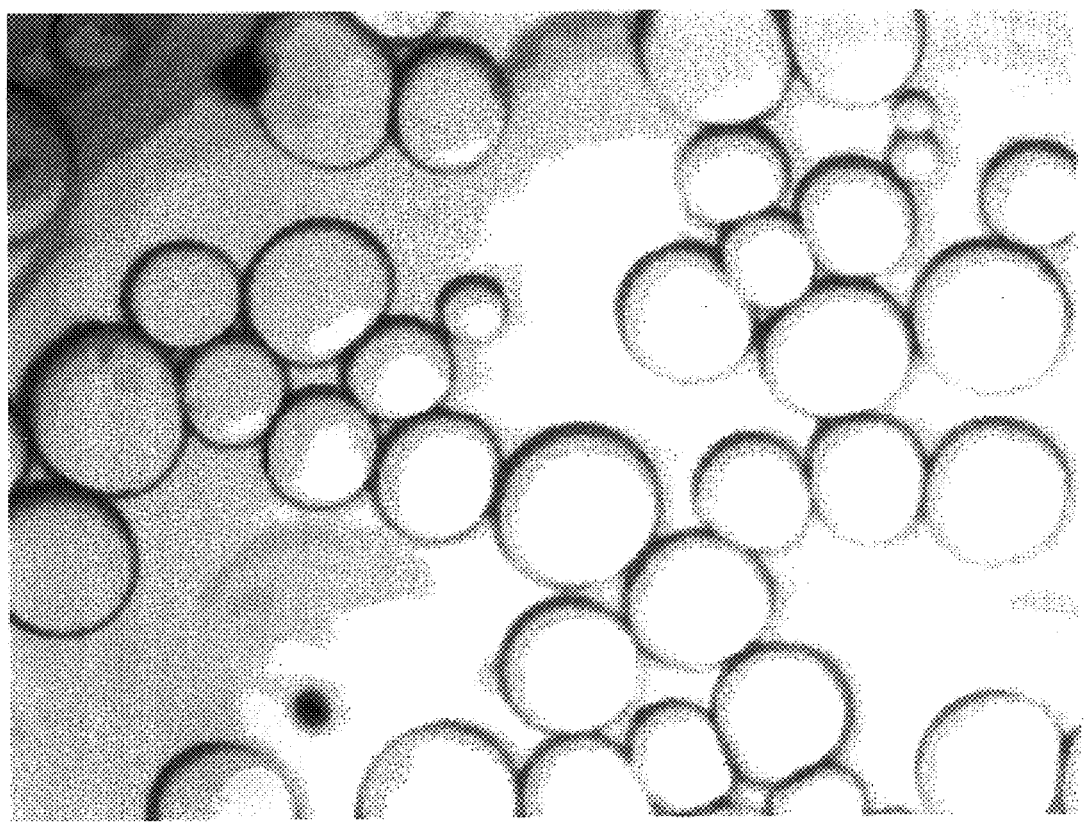

(8) A 42% reduction in basal lipolysis from isolated adipocytes (FIG. 11) of in vivo treated mice with no change in glucose transport (FIG. 10A) or oxidation (FIG. 10B) or GLUT4 expression (data not shown) as well as a significant reduction in adipocyte size (Compare FIGS. 13B and 13A).

Figure 12A:
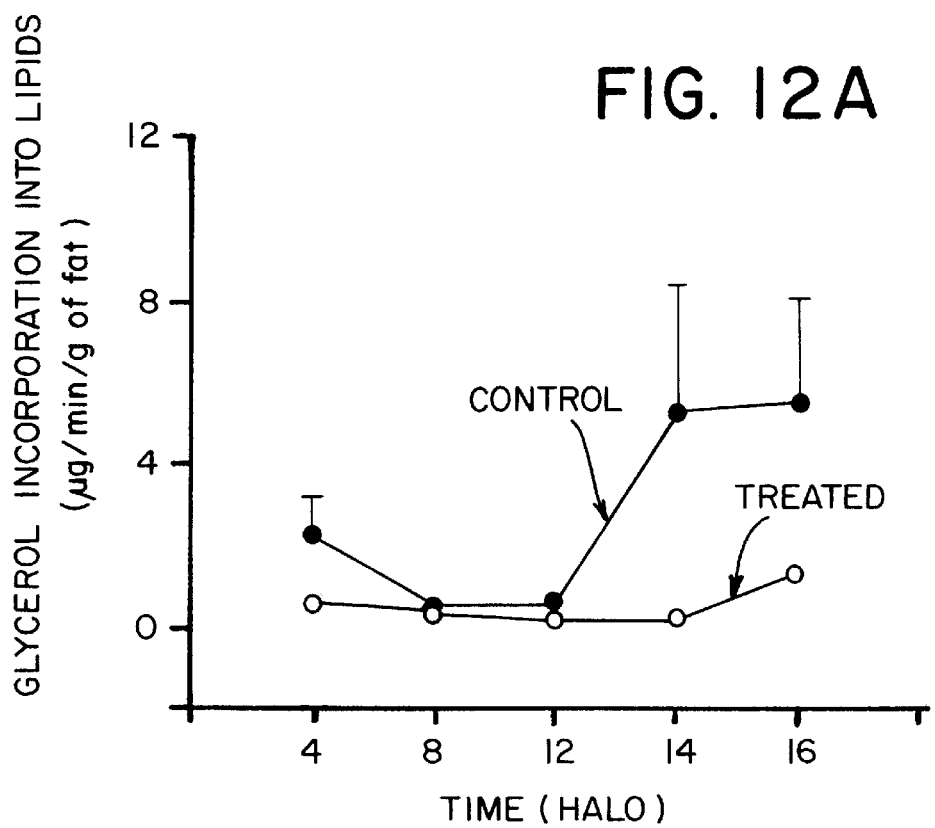
FIGS. 12A is a graph of adipose lipogenesis measured as rate of glycerol incorporation into lipids (mg/minute/gram of fat) as a function of the sacrifice time for mice (in HALO) treated with BC+SKF (open circles) or not treated (dark circles).
Figure 12B:
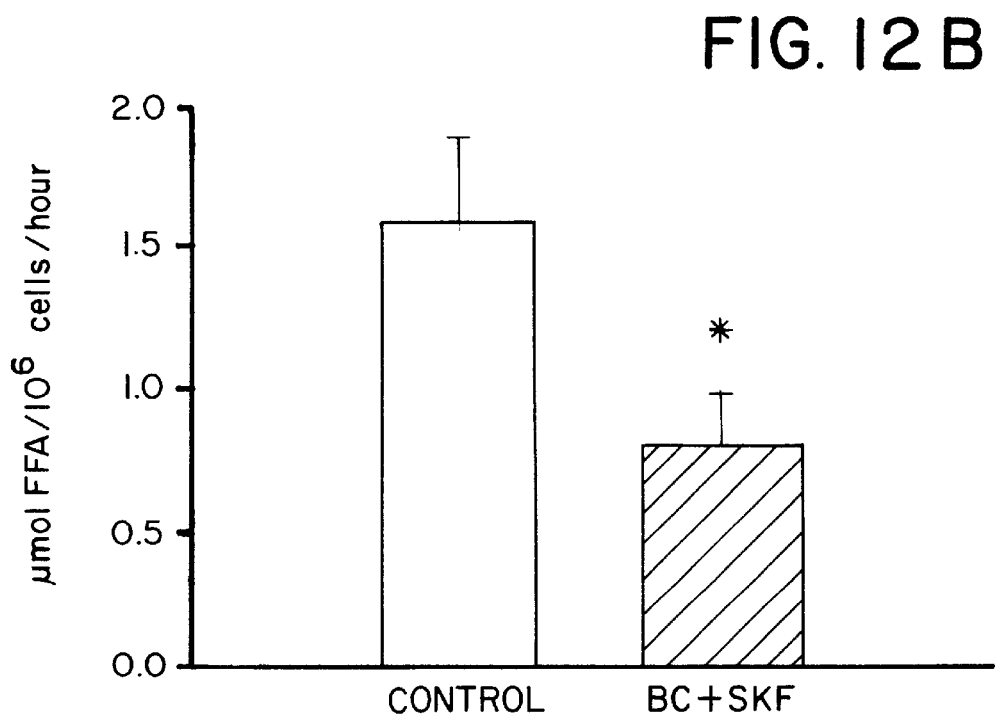
FIG. 12B is a bar graph of lipoprotein lipase (LPL) activity (in mmol of free fatty acid/$10^6$ cells/hour for SKB+ BC treated or "no drug" mice.

(9) A 50% reduction in adipose tissue lipoprotein lipase (LPL) activity and a blocking of lipogenesis (FIGS. 12B and 12A respectively).

Figure 14A:
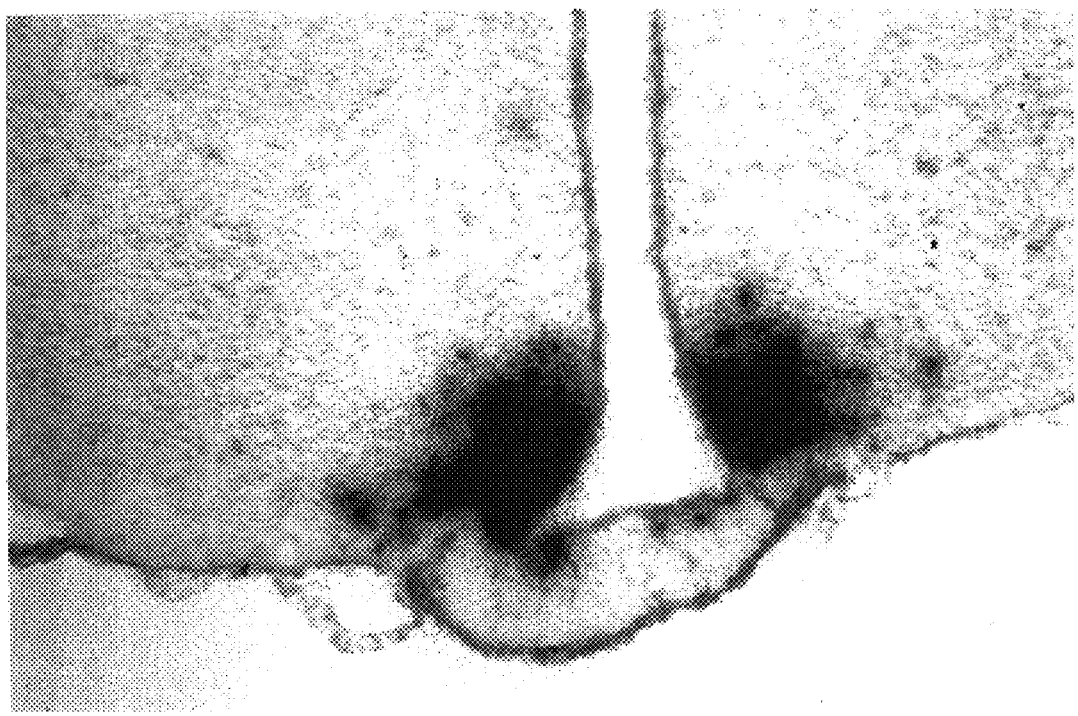
FIGS. 14A–14C are photomicrographs of arcuate nuclei of ob/ob control mice (FIG. 14A) ob/ob BC+SKF treated mice (FIG. 14B) and lean (57 BL/6J) controls (FIG. 14C) showing large amounts of neuropeptide Y (NPY) mRNA in the ob/ob controls and significantly reduced amounts of NPY mRNA in the ob/ob treated mice.
Figure 14B:
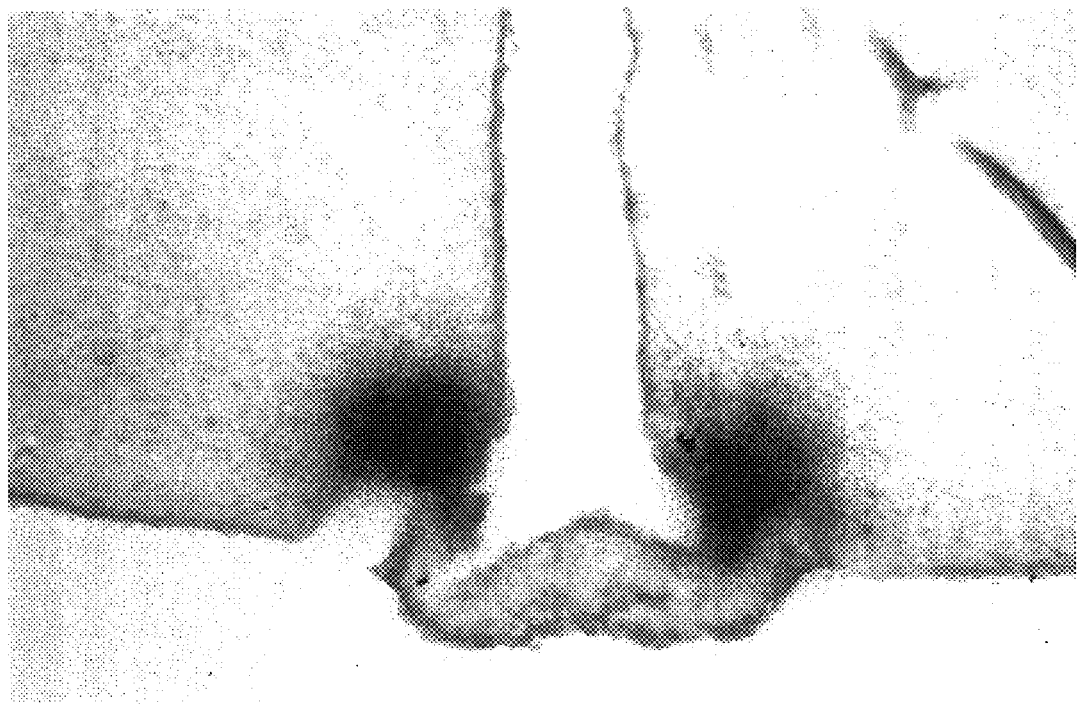
Figure 14C:
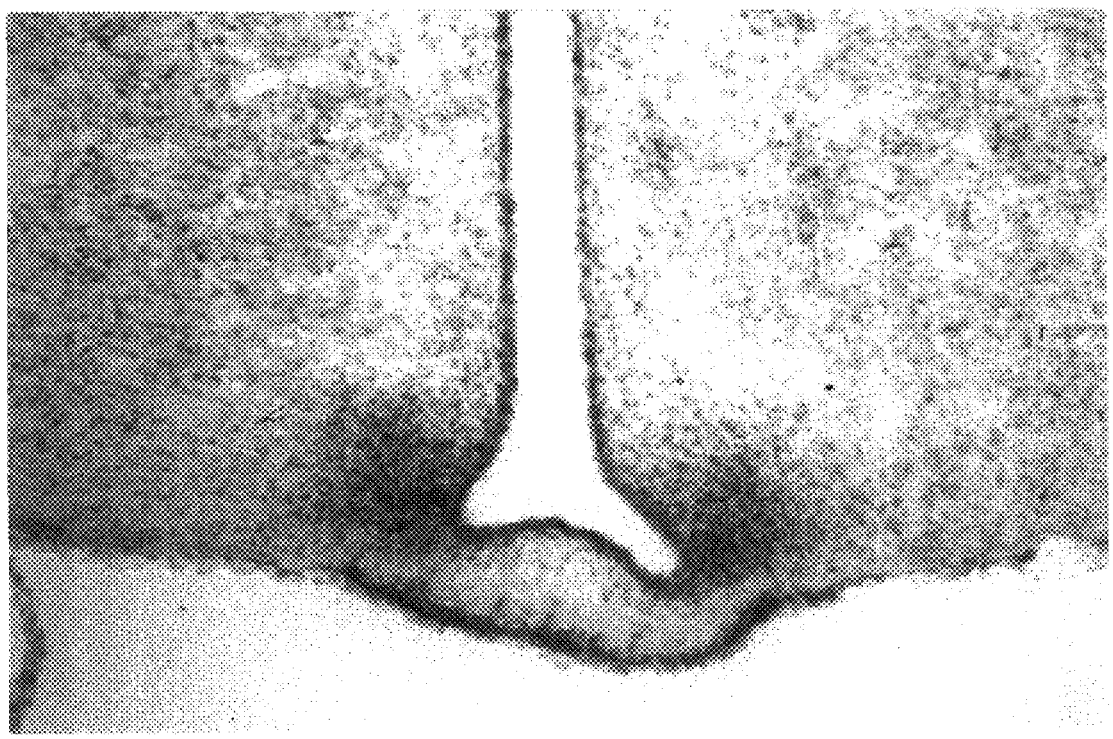
Figure 15:
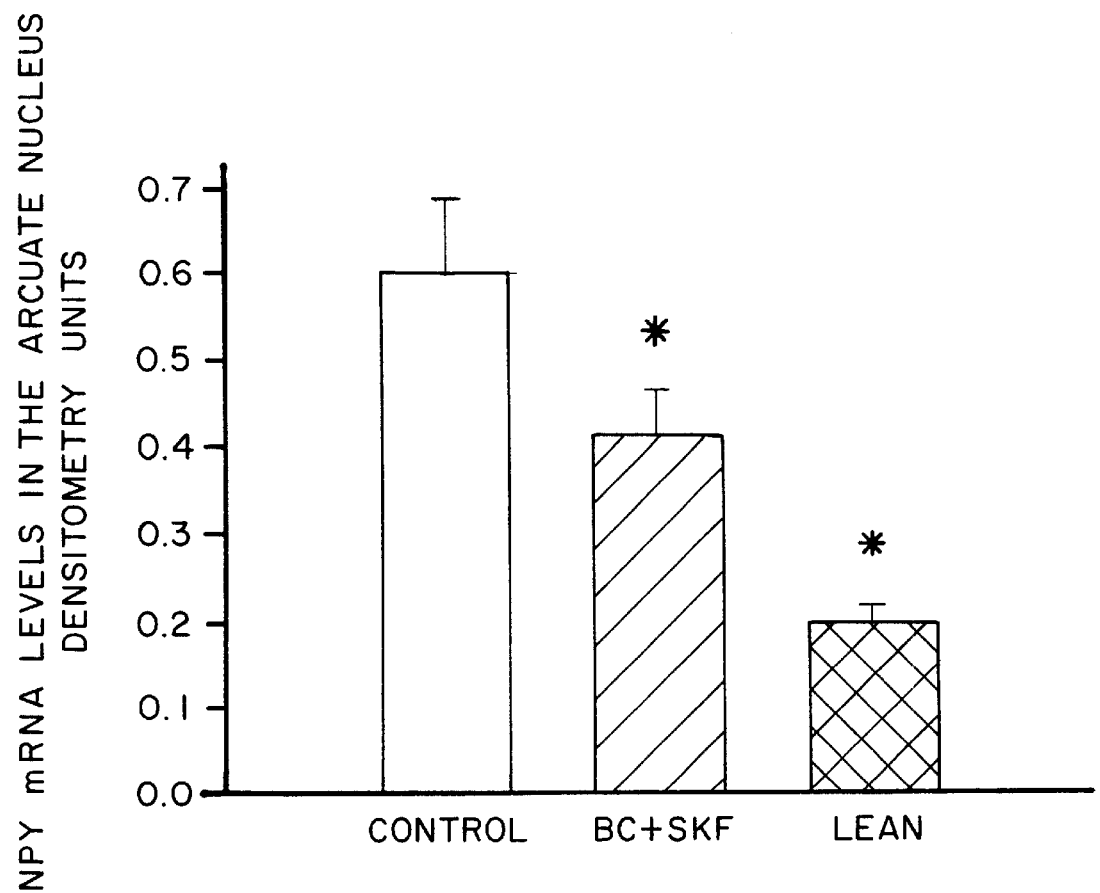
FIG. 15 is a bar graph of NPY mRNA in the arcuate nucleus of ob/ob mice treated with BC+SKF (middle bar) or untreated ob/ob mice (left bar) or untreated lean controls (right bar).

(10) The observed metabolic changes induced by BC+SKF are associated with a 30% reduction in NPY mRNA level within the arcuate nuclei resulting in levels still two fold greater than in lean (+/+) counterparts (FIG. 15). A similar result can be qualitatively observed in FIGS. 14A–14C.

Figure 6A:
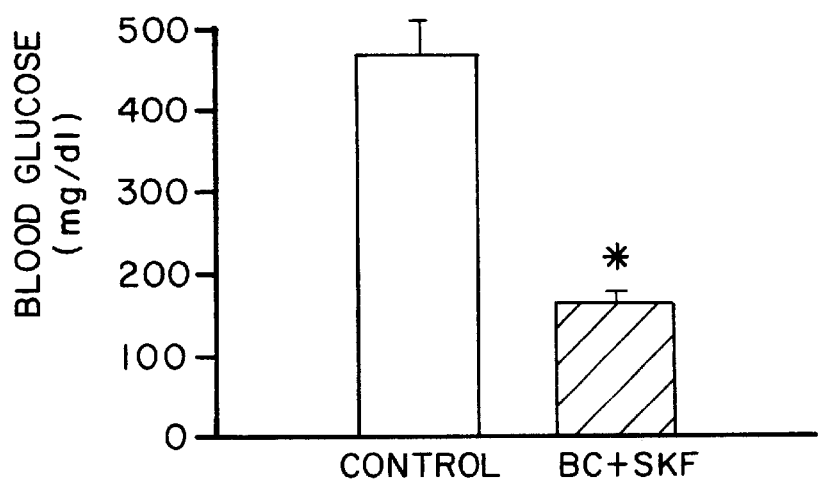
FIGS. 6A–6C are bar graphs of blood glucose levels in mg/dl (FIG. 6A) serum triglyceride levels in mg/dl (FIG. 6B) and serum FFA in mmol/l (FIG. 6C) for animals administered no drug (left bar) or both BC and SKF (right bar). The asterisks have the same significance as for FIG. 3A. The animals were sacrificed at 3 HALO the lipogenesis peak for mice.
Figure 6B:
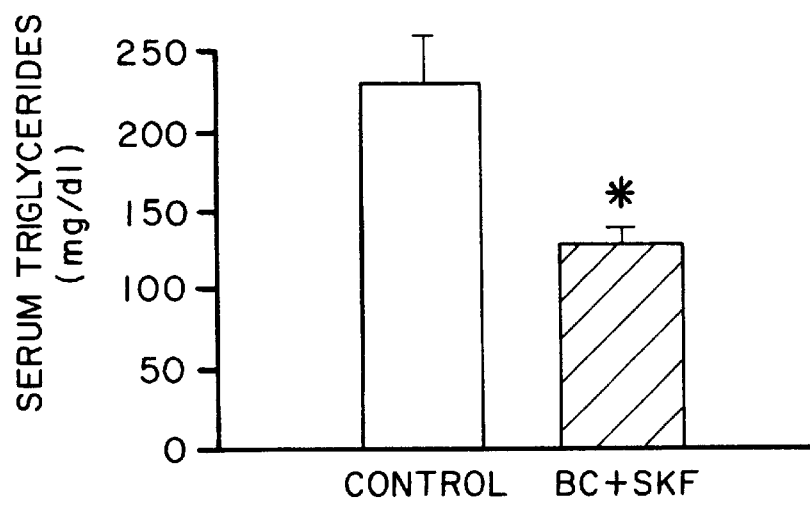
Figure 6C:
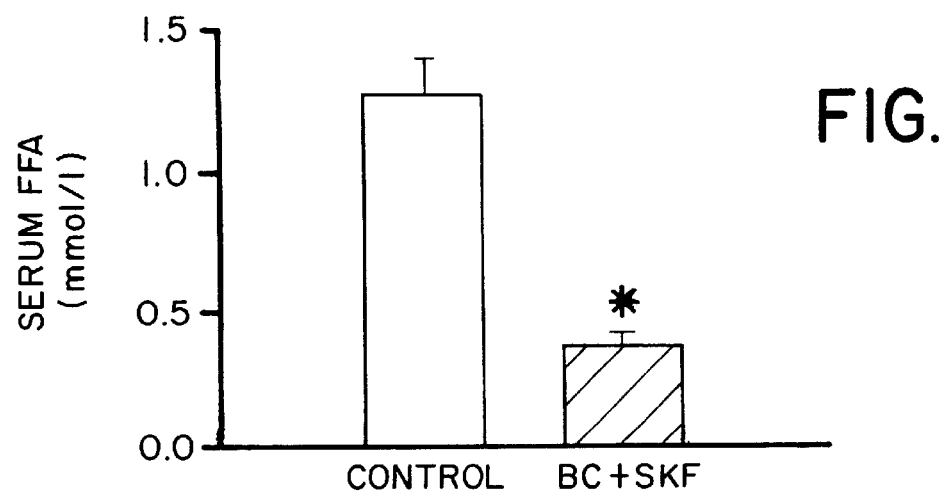

(11) The reduction in blood glucose, triglyceride and free fatty acid is more pronounced at 4 HALO (peak of lipolysis in the mouse). See FIG. 6 and compare FIG. 6A with FIG. 4A, FIG. 6B with FIG. 5A and FIG. 6C with FIG. 5B.

Treatment of genetically obese C57 BL/6J mice with bromocriptine ($D_2$ agonist) plus SKF38393 ($D_1$ agonist) induced a reduction of body weight associated with a marked (42%) reduction of hyperphagia. The resulting weight loss was attributed nearly exclusively to loss of fat with protein mass remaining unchanged or even increased. Fat loss may be attributed to decreased caloric intake as well as decreased lipogenesis as both hepatic and adipose lipogenic enzyme activities were reduced by treatment. The substantial reduction in caloric intake induced by treatment was associated with a large reduction in circulating free fatty acids (FFA). That is, fat cell size (lipid content) decreased appreciably while lipogenesis and lipid mobilization concurrently decreased. Apparently, the decreased mobilization is associated with an even greater decrease in lipid accretion. Such a conclusion is supported by the findings of decreased adipose LPL, and serum total and VLDL-TG (very low density lipoprotein/triglycerides).

The marked reduction in serum glucose induced by treatment is associated with a strong reduction in hepatic glucose-6-phosphatase activity and a somewhat less dramatic decrease in phosphoenolpyruvate carboxykinase activity. Interestingly, the reduction in hepatic G-6-phosphatase activity and the simultaneous increase in G-6-P dehydrogenase activity suggest specific metabolic channelling towards glucose utilization in the liver rather than glucose release or production. Such alterations in liver metabolism facilitate increase of hepatic HADPH, nucleic acid, and protein synthesis.

The foregoing findings may be applied to treatment of humans suffering from obesity and other lipid disorders.

EXAMPLE 2

Figure 16:
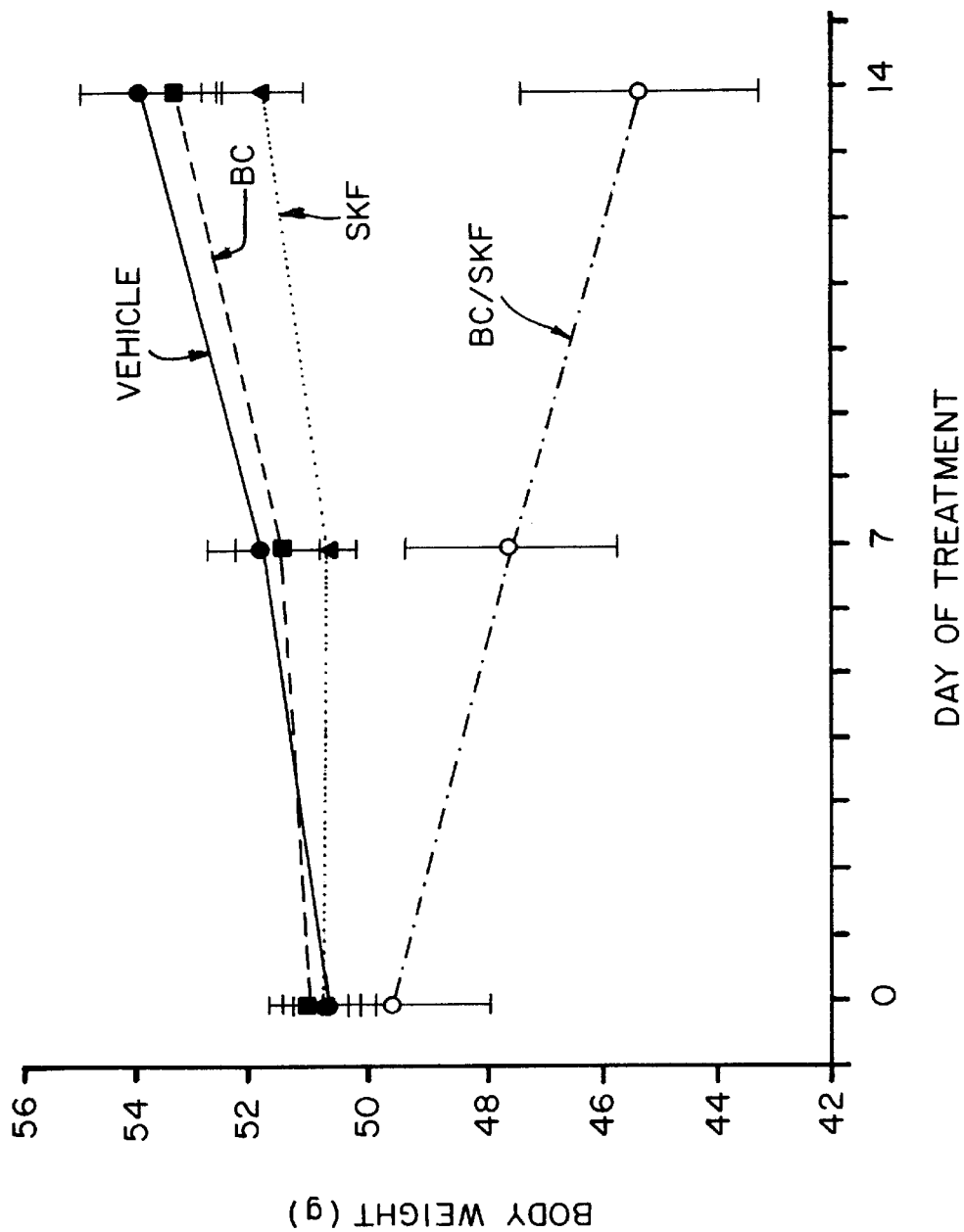
FIG. 16 is a plot of body weight v. day of treatment with a $D_2$ agonist alone or with $D_1$ agonist alone or with a combination of $D_1/D_2$ according to the invention. BC (10 mg/kg), BC plus SKF 38393, or vehicle injection on body weight in C57BL/6J ob/ob mice during two weeks of daily treatment at 1 hour after light onset. An asterisk denotes a significant difference in body weight change relative to all other treatment groups ($P<0.02$).

Different groups of 6-week old C57BL/6 ob/ob mice (lacking a functional leptin protein) were treated with either bromocriptine ("BC") (10 mg/kg BW), SKF38393 ("SKF") (10 mg/kg BW), both drugs, or vehicle for two weeks at 1 hour after light onset (HALO). Animals were held on 12-hour daily photoperiods and allowed to feed ad libitum. Food consumption was monitored daily for 3 days before the initiation of treatment throughout the 14-day treatment period. Animals were sacrificed between 1 and 3 HALO on the day following the final treatment (i.e., 24–26 hours after last injection) and plasma was collected for the analyses of insulin, glucose, and lipids while the carcasses were solubilized in ethanolic KOH and analyzed for protein and lipid content. Bromocriptine and SKF38393, individually, were ineffective in reducing body weight gain where as SKF, but not BC, reduced food consumption (19%, P<0.01). However, the combined treatment of bromocriptine and SKF38393 (BC/SKF) decreased food consumption by 46% (from 4.8±0.2 to 2.6±g/day; P<0.001) and body weight by 15% (from a 3.2 g increase in controls to a 4.3 g decrease; P<0.005) in 14 days of treatment (FIG. 16). Relative to controls, in absolute terms, the lipid content of the BC/SKF treated animals was decreased by 40% (from 4.2±0.2 to 2.5±0.3 g glycerol/animal; P<0.0003) whereas the protein content increased 8% (from 3.7±0.08 to 4.0±0.08 g/animal; P<0.05). Therefore, relative to control mice, the BC/SKF treated animals consumed less food but actually increased protein mass while concurrently losing weight and fat. This effect on body composition was observed by SKF (P<0.003)

or BC (P<0.04) treatments alone, although to a lesser extent than by BC/SKF combination (P<0.05). Although BC alone and SKF alone significantly reduced plasma glucose concentration (by 31%; P<0.02 and 43%; P<0.004, respectively), the BC/SKF combination reduced plasma glucose (by 60%; P<0.0004) substantially more than either drug alone (P<0.03) to values equivalent to those values reported for lean euglycemic C57BL/6 mice (+/+)(1). Plasma insulin level was equally reduced by BC and BC/SKF treatment (50%; P<0.04), but was not affected by SKF alone. BC/SKF, but neither BC nor SKF individually, reduced plasma triglyceride and free fatty acid levels (by 36%; P<0.05 and 44%; P<0.007), (Table 1, below). These data indicate that the interactive effects of BC and SKF effectively reduced hyperphagia, obesity, insulin resistance, hyperglycemia, hyperinsulinemia, and hyperlipidemia in the ob/ob mouse.

normalizing its circadian rhythm. Such effects demonstrate the involvement both of circadian systems and BC/SKF influence on these systems in the regulation of metabolism.

EXAMPLE 4

The effect of in vivo BC/SKF treatment on glucose induced insulin release was studied in vitro. Obese (ob/ob) and lean (+/+) C57BL/6J mice were treated daily for 2 weeks with BC (10 mg/kg) plus SKF (20 mg/kg) or vehicle only. Mice were sacrificed 25 hours after the final treatment and islets were isolated for static incubation with glucose. The BC/SKF treatment of obese mice reduced blood glucose (173±14 mg/dl, P<0.01), plasma total glycerol 162±9 vs. 386±33 mg/dl, P<0.01), and plasma total cholesterol (143±5 vs. 184±5 mg/dl, P<0.01) relative to obese controls. The plasma free fatty acid and insulin levels of treated mice were also reduced by 20–30% compared with that in obese

TABLE 1

Effects of BC (10 mg/kg), SKF (10 mg/kg), BC plus SKF, or vehicle injections at 1 HALO on body weight, carcass composition, food consumption, and plasma glucose, insulin, and lipid levels of ob/ob mice following two weeks of treatment. Animals were sacrificed 24–26 hours following last treatment. Within parameters, values with similar superscripts denote a significant difference between treatments (P < 0.05 to < 0.0001).

|  | Final Body Weight (g) | Whole Body Lipid-Glycerol (g) (% BW) | Whole Body Protein (g) (% BW) | Plasma Glucose (mg/dl) | Plasma Insulin (ng/ml) | Plasma TG (mg/dl) | Plasma FFA (uM) | Food Consumption (g/day) |
|---|---|---|---|---|---|---|---|---|
| CONTROL | $54 \pm 1^1$ | $4.2 \pm 0.2^1$ <br> $7.9 \pm 0.3^1$ | $3.7 \pm 0.1^{1,2,3}$ <br> $6.9 \pm 0.2^1$ | $380 \pm 39^{1,2}$ | $59 \pm 12^{1,2}$ | $313 \pm 49^1$ | $825 \pm 83^1$ | $48 \pm 0.2^{1,4}$ |
| BC | $53 \pm 0.7^2$ | $3.7 \pm 0.1^1$ <br> $7.0 \pm 0.2^1$ | $4.0 \pm 0.1^1$ <br> $7.5 \pm 0.1^1$ | $262 \pm 25^1$ | $30 \pm 4^2$ | $405 \pm 101$ | $818 \pm 64^2$ | $4.5 \pm 0.2^{2,5}$ |
| SKF | $52 \pm 0.7^1$ | $3.1 \pm 0.1^1$ <br> $6.0 \pm 0.2^1$ | $4.1 \pm 0.04^2$ <br> $7.9 \pm 0.1^1$ | $218 \pm 22^2$ | $50 \pm 13$ | $234 \pm 22^1$ | $671 \pm 36^3$ | $3.9 \pm 0.07^{3,4,5}$ |
| BC/SKF | $45 \pm 2^{1,2,3}$ | $2.5 \pm 0.3^1$ <br> $5.4 \pm 0.5^1$ | $4.0 \pm 0.1^3$ <br> $8.8 \pm 0.04^1$ | $154 \pm 15^{1,2}$ | $30 \pm 9^1$ | $199 \pm 18$ | $461 \pm 63^{1,2,3}$ | $2.6 \pm 0.2^{1,2,3}$ |

Values differ significantly from obese controls (a = P < 0.05; b = P < 0.01; c = P < 0.001).

EXAMPLE 3

The effects of BC/SKF treatment on circadian rhythms of key metabolic enzyme activities, serum metabolites and hormones regulating metabolism were examined. Obese C57BL/6J mice were treated for 2 weeks at 1 hour after light onset with BC (10 mg/kg BW) and SKF (20 mg/kg BW) or vehicle. Mice were then sacrificed every 4 hours over a 24 hr period for the analyses of serum hormones and metabolites and hepatic enzymatic activities. Serum glucose, free fatty acid (FFA) and hepatic glucose-6-phosphatase (G6Pase) activity were greatest during the light period of the day showing that this time period is the daily peak for lipolysis and hepatic glucose production in mice. BC/SKF treatment significantly reduced blood glucose (51%), FFA (56%) and G6Pase activity (38%) during this light period. Moreover, serum levels of the lipolytic and gluconeogenic hormones thyroxine and corticosterone were also highest during the light period and their levels were significantly reduced by 51% and 53%, respectively by BC/SKF treatment. BC/SKF treatment also decreased the daily peak in liver phosphoenol pyruvate carboxykinase activity by 27% and increased the daily peak in liver glucose 6 phosphate dehydrogenase (by 32%) (potentiating glycolysis via xylose-5-phosphate production). Levels of serum insulin and liver malic enzyme were greatest during the dark period (feeding time) of the day illustrating increased lipogenesis during this time in mice. During this dark period BC/SKF treatment reduced serum insulin significantly, i.e., by 42%, and liver malic enzyme by 26%. BC/SKF treatment also decreased liver fatty acid synthase activity by 30–50%, controls. In control ob/ob mice, the insulin release from isolated islets stimulated by 10 mM glucose was the same as that by 8 mM glucose (1.6±0.2 vs. 1.9±0.5 ng/islet/h), while in BC/SKF treated ob/ob mice, 15 mM glucose induced a significant increase of insulin release compared with 8 mM glucose (4.1±0.8 vs. 1.8±0.4 ng/islet/h, P<0.05). This enhancement is comparable to that observed in lean mice which exhibited a 2 fold increase of insulin release in response to 15 mM vs. 8 mM glucose. Similar BC/SKF treatment of lean mice showed no effect on glucose-stimulated insulin release from isolated islets compared to lean controls. BC/SKF treatment reversed impaired islet glucose sensing in ob/ob mice possibly due in part to the improvement of hyperglycemia and hyperlipidemia by this treatment.

Since hyperglycemia and hyperlipidemia may induce islet desensitization to glucose, which is a common syndrome in obesity-associated NIDDM in humans, the above finding can be applied to therapy of NIDDM in humans.

EXAMPLE 5

Metabolic changes resulting from the $D_1/D_2$ agonist treatment were evaluated in mice to determine if they were accompanied by decreases in density of NPY immunoreactivity in discrete hypothalamic nuclei. Female ob/ob mice (30–35 g) were treated daily at 1 h after light onset with SKF38393 (20 mg/kg) and bromocriptine (15 mg/kg) or vehicle. Lean mice (C57BL/6J; 18–21 g) treated with vehicle also served as controls. Following treatment for 12 days mice were sacrificed and their brains processed for NPY immunoreactivity. The treatment (summarized in Table 2 below) produced a significant decline in NPY levels in the SCN (38.5% P<0.01), the arcuate nucleus (41%; P<0.005) and the PVN (31.4% P<0.05) compared to obese controls. In addition, during the study body weights increased in obese controls (8.3+/−0.9 g) whereas it decreased in treated animals (−1.1+/−2 g) (P<0.0001). These results indicate that time of day-dependent dopaminergic $D_1/D_2$ coactivation improves hyperphagia, hyperglycemia and obesity in the ob/ob mouse, in part, by reducing elevated levels of hypothalamic NPY to that of lean animals.

TABLE 2

| Type | Food consumed (g/day) | Blood glucose (mg/dl) | NPY density (arbitrary units) | | |
|---|---|---|---|---|---|
| | | | SCN | Arcuate | PVN |
| Lean | 3.1 +/− 0.1 | 133 +/− 5 | 39.8 +/− 3 | 54 +/− 4 | 49 +/− 5 |
| Obese | 6.1 +/− 0.1 | 216 +/− 16 | 55.2 +/− 4 | 95 +/− 10 | 52 +/− 6 |
| Treated | 4.3 +/− 0.1[c] | 136 +/− 9[c] | 34 +/− 4[b] | 56 +/− 8[b] | 36 +/− 3[a] |

EXAMPLE 6

The influence of BC/SKF treatment on hepatic glucose metabolism was examined. Female C57BL/6J obese (ob/ob) mice (BW=46±1 g) were treated daily for 2 wks with BC (12.5 mg/kg) and SKF (20 mg/kg) or vehicle (n=8–12/group) at 1 hr after light onset and then sacrificed at 24–26 hrs following the final day of treatment and liver tissue removed and analyzed for glucose 6-phosphatase (G6Pase) and glucose 6 phosphate dephdrogenase (G6PDase) activities and hepatic xylose-5-phosphate (X5P) concentration. Serum glucose and insulin levels were also determined. BC/SKF treatment significantly (P<0.01) reduced serum glucose by 57% (from 435±21 to 185±8 mg/dl), serum insulin by 44% (from 25±2 to 14±3 ng/ml), hepatic G6Pase activity by 67% (from 1.5±0.3 to 0.5±0.07 $\mu$moles/min/mg), and increased hepatic G6PDase activity by 73% (from 11±1 to 19±3 nmoles/min/mg), and X5P concentration by 73% (from 166±10 to 287±30 nmoles/g) relative to control. BC/SKF treatment resulted in a gluconeogenic substrate being shuttled away from glucose to the pentose phosphate pathway by the simultaneous inhibition of glucose 6-phosphatase (G6Pase) and stimulation of glucose-6-phosphate dephdrogenase (G6PDase) thereby respectively blocking hepatic glucose production and shuttling glucose-6-phosphate towards production of xylose-5-phosphate (X5P), a potent activator of glycolysis. This is the first study to identify the existence of such a biochemical shift in hepatic glucose metabolism and its regulation by dopaminergic activation. Moreover, this dopaminergic regulated shift from hepatic gluconeogenesis towards potentiation of glycolysis could contribute to the normalization of severe hyperglycemia in these animals and may have significance in both the development and treatment of NIDDM in humans. Available evidence suggests that BC/SKF is acting in part at the ventromedial hypothalamus to produce these effects.

EXAMPLE 7

The combination of hyperglycemia and hypertriglyceridemia has been implicated as a risk factor for cardiovascular disease in NIDDM. Dopaminergic $D_1/D_2$ receptor co-activation with SKF38393 (SKF), a $D_1$ receptor agonist, plus bromocriptine (BC), a $D_2$ receptor agonist has been shown to act synergistically to reduce obesity. Its effects on hyperglycemia, dyslipidemia, and plasma lipoprotein dynamics were tested in ob/ob mice. Obese C57BL/6J (ob/ob) mice (BW) 44.5±0.5 g) were treated daily at light onset with vehicle (control) or SKF (20 mg/kg BW) plus BC (16 mg/kg BW) for 14 days. 25 to 28 hrs following the final treatment, animals were sacrificed and blood was collected for lipoprotein fractionation and analysis. Lipoprotein and serum triglyceride (TG), cholesterol (CH), phospholipid (PL), and serum glucose, insulin, and free fatty acid (FFA) were measured. White adipose, skeletal muscle, and heart tissues were harvested for analysis of lipoprotein lipase (LPL) activities. A second group of similarly treated animals was utilized for determination of hepatic triacylglycerol synthesis by following $^3$H-glycerol incorporation into liver triglyceride 30 mins after its administration in vivo. 14 days of SKF/BC treatment significantly reduced blood glucose (390±17 to 168±6 mg/dl), serum TG (397±22 to 153±7 mg/dl), CH (178±4 to 139±4 mg/dl), PL (380±7 to 263±11 mg/dl), and FFA (1.1±0.1 to 0.7±0.1 mmol/1) (P<0.01). Insulin was also reduced from 40±5 to 28±4 ng/ml (P=0.058). Chylomicron-TG and VLDG-TG were reduced from 228±2 to 45±6 mg/dl and 169±7 to 110±4 mg/dl respectively (P<0.01). Hepatic triacylglycerol synthesis was reduced by 47% (P<0.01). LPL activity was unchanged in skeletal and heart muscle tissues but was sharply reduced (67%) in adipose tissue (P<0.01). LDL cholesterol level was reduced by 31% (P<0.01). These data indicate that SKF/BC normalized hypertriglyceridemia via 1) decreasing Chylomicron-TG level and 2) decreasing VLDL-TG synthesis and secretion. The marked decrease in adipose LPL activity further supports the conclusion that serum VLDL-TG is reduced by decreased hepatic synthesis rather than increased removal from the circulation and may also contribute to the decreased serum FFA level. Moreover, the decreased serum FFA may contribute to the decreased hyperglycemia.

EXAMPLE 8

A 2-week treatment with SKF38393 (SKF), a dopamine $D_1$ receptor agonist, and bromocriptine (BC), a dopamine $D_2$ receptor agonist acts synergistically to reduce body fat and hyperglycemia in ob/ob mice in a food consumption independent manner. The biochemical mechanisms responsible for this effect were evaluated by measuring energy expenditure and metabolic substrate utilization determined from respiratory quotient (RQ) of treated versus control mice. Circulating free fatty acid (FFA) levels represent the major rate limiting factor for fat oxidation and increased FFA also potentiate hyperglycemia in insulin resistant states. The influence of in vivo treatment with SKF38393 (SKF), a dopamine $D_1$ receptor agonist, and bromocriptine (BC), a dopamine $D_2$ receptor agonist, on serum FFA level and in vitro lipolysis in isolated adipocytes was tested. C57BL/6J obese (ob/ob) female mice were treated with vehicle (control) or SKF k(20 mg/kg BW) plus BC (10 mg/kg BW) for 14 days. BC/SKF treatment increased $O_2$ consumption and $CO_2$ production by 143% and 90% respectively (P<0.0001). Moreover, RQ values were shifted by treatment from 1.55±0.35 to 1.03±0.11 indicating a decrease in de novo glucose conversion to lipids (lipogenesis) and nearly exclusive utilization of glucose as an energy source (i.e., little fat oxidation). These findings are in accord with the substantial drug-induced decrease in serum glucose level (489±25 to 135±10 mg/dl, P<0.0001). These conclusions from the RQ data are further supported by a dramatic decrease in fat cell size (from 0.722±0.095 to 0.352±0.03 $\mu$g of lipid/cell, P<0.02) and a marked reduction in serum FFA levels (from 1.06±0.1 to 0.32±0.02 mM, P<0.001) and in vitro isoproterenol stimulated lipolysis (from 16.4±2.4 to 5±0.6 pmoles of glycerol released/cell/20 min, P<0.005). Therefore, the dramatic increase in $O_2$ and $CO_2$ production (and decreased fat cell size) cannot be explained by increased fat mobilization and oxidation. These data indicate that dopaminergic $D_1, D_2$ receptor coactivation shifts glucose metabolism from lipogenesis to oxidation with a concurrent decrease of fat mobilization and oxidation (thereby possibly improving insulin sensitivity). These findings have significance for the treatment of obesity and hypertriglyceridemia associated with NIDDM.

EXAMPLE 9

The combined effectiveness of SKF38393 (SKF), a $D_1$ receptor agonist, and bromocriptine (BC), a $D_2$ receptor agonist, were examined in treating obesity and diabetes in ob/ob (mice lacking the gene for the leptin protein) and db/db (mice lacking the gene for the leptin receptor) mice. Daily drug injections were administered to female C57BL/6J ob/ob and C57BL/KJ db/db mice 1 hr after light onset for 14 days. Drug treated groups received BC (16 mg/kg) plus SKF (20 mg/kg), whereas pair fed groups (food adjusted to drug treated groups' intake) and control groups received the vehicle. Oxygen consumption was measured in metabolic cages on day 11 or 12 of treatment. Plasma glucose, FFA, and insulin levels, were measured on day 14. In the ob/ob mice statistically significant results included: controls gained 6.9±1.3 g of body weight, while the treated mice lost 7.4±0.4 g. The average daily food consumption of controls was 6±0.2 g versus 2.8±0.1 g of treated. Oxygen consumption for controls and treated was 1277±240 ml/kg/hr and 1623±230, respectively. Plasma glucose levels were 471±42 mg/dl in controls, and 164±13 in treated. k FFa levels were 1.27±0.1 mM in controls, and 0.37±0.05 in treated. Plasma insulin were 63.5±17 ng/ml in controls, and 37.3±6.6 in treated. Similar statistically significant results were observed in db/db mice: controls gained 6.6±0.4 g, of body weight versus 3.4±1.3 g in the treated. The average daily good consumption of controls was 10.7±2.8 g versus 5.9±0.5 g of the treated. Oxygen consumption for control and treated was 898±2150 ml/kg/hr and 2322±283, respectively, Plasma glucose levels were 485±29 mg/dl in controls, and 390±55 in the treated. FFA levels were 1.49±0.2 mM in controls, and 0.45±0.04 in treated. Plasma from pairfed animals (in both ob/ob and db/db mice) indicate that the above drug-induced metabolic changes are not primarily the consequence of decreased food consumption. These results strongly suggest that hyperphagia, hyperglycemia and hyperlipidemia in animals lacking either leptin (ob/ob) or a functional leptin receptor (db/db) can be treated with the combined administration of $D_1$ and $D_2$ receptor agonists.

EXAMPLE 10

Pharmacological intervention with bromocriptine improves glucose and lipid metabolism in NIDDM animals and patients. The influence of such treatment on pancreatic islet function was investigated. The effect of $D_1/D_2$ receptor agonists—bromocriptine/SKSF38393 (BC/SKF) on islet function in a mouse diabetic model was evaluated. Female db/db mice (30±1 g) were treated daily for 2 weeks at 1 hr after light onset with 1) BC (16 mg/kg) plus SKF (20 mg/kg), 2) vehicle only (controls), or 3) vehicle plus feed restriction to match the reduced food consumption of treated mice (pair fed). The BC/SKF treatment reduced blood glucose (347±28 vs. 606±31 mg/dl in controls, P<0.01) and plasma free fatty acids (0.6±0.1 vs. 1.1 k+0.1 mM in controls, P<0.01) levels, and increased plasma insulin level by 3-fold compared with that in controls (49±5 vs. 16±2 ng/ml, P<0.01). In pair fed mice there was a more modest (30%) reduction (P<0.01) of blood glucose but no change in plasma insulin and a 20% increase in plasma free fatty acids compared with control levels. The insulin release response of pancreatic islets to secretagogue was tested in vitro. Insulin release from incubated islets stimulated by glucose (8 and 15 mM), arginine (10 mM) and acetylcholine (10 uM) was each 3–4 fold greater in the treated group compared with that in controls (P<0.05). Contrariwise, secretagogue-induced insulin release from incubated islets of pair fed mice were similar to those in controls. Furthermore, similar BC/SKF treatment had no effect in normal mice. Addition of BC/SKF directly to the islet incubation buffer did not enhance insulin release from db/db mouse islets. These results demonstrate the BC/SKF given in vivo markedly enhance islet function in the db/db but not the normal mouse. This effect is not attributable to either a direct action on islet function or inhibition of feeding.

What is claimed is:

1. A method for modifying or regulating at least one of glucose or lipid metabolism disorders which comprises administering to a human or vertebrate animal subject in need of such modification or regulation D1 dopamine agonist 1-phenyl-2,3,4,5-tetrahydro-[1H]-benzazepine-7,8-diol, or a pharmaceutically acceptable salt thereof, in conjunction with an ergot alkaloid dopamine D2 agonist wherein the conjoined administration is effective to improve at least one of the following lipid and glucose metabolic indices: body weight, body fat, plasma insulin, plasma glucose and plasma lipid, and plasma lipoprotein.

2. The method of claim 1 wherein the D2 agonist is an ergot alkaloid selected from the group consisting of 2-bromo-α-ergocriptive, 6-methyl-8-β-carbobenzyloxy-aminoethyl-10-α-ergoline, 8-acylaminoergoline, pergolide, lisuride, 6-methyl-8-α-(N-acyl)amino-9-ergoline, 6-methyl-8-α-(N-phenyl-acetyl)amino-9-ergoline, ergocomine, 9,10-dihydroergocomine, D-2-halo-6-alkyl-8-substituted ergolines, and D-2-bromo-6-methyl-8-cyanomethylergoline or a pharmaceutically acceptable salt thereof.

3. The method of claim 2 wherein the ergot alkaloid comprises bromocriptine or a pharmaceutically acceptable salt thereof.

4. The method of claim 3 wherein said glucose or lipid metabolism disorder is selected from the group consisting of type 2 diabetes, obesity, and hyperlipoproteinemia.

5. The method of claim 3 wherein the bromocriptine is administered at a predetermined time of the day.

6. The method of claim 5 wherein said predetennined time of day is between about 7:00 and 12:00.

7. The method of claim 6 wherein the D1 agonist is administered at about the same time as the D2 agonist.

8. The method of claim 7 wherein said glucose or lipid metabolism disorder is selected from the group consisting of type 2 diabetes, obesity, and hyperlipoproteinemia.

9. The method of claim 5 wherein the D1 agonist is administered at about the same time as the D2 agonist.

10. The method of claim 1 wherein the D2 agonist is administered at a predetermined time of day.

11. The method of claim 10 wherein the D1 agonist is administered at about the same time as the D2 agonist.

12. The method of claim 10 wherein said predetermined time of day is between about 7:00 and 12:00.

13. The method of claim 12 wherein the D1 agonist is administered at about the same time as the D2 agonist.

14. The method of claim 1 wherein said glucose or lipid metabolism disorder is selected from the group consisting of type 2 diabetes, obesity, and hyperlipoproteinemia.

* * * * *

UNITED STATES PATENT AND TRADEMARK OFFICE
CERTIFICATE OF CORRECTION

PATENT NO. : 6,855,707 B2
DATED : February 15, 2005
INVENTOR(S) : Anthony H. Cincota It is certified that error appears in the above-identified patent and that said Letters Patent is hereby corrected as shown below:

<u>Title page,</u>
Item [75], Inventor, please delete "Anthony H. Cincotta, Charlestown, MA (US)" and substitute with -- Anthony H. Cincotta, Tiverton, RI (US) --.

Signed and Sealed this

Seventeenth Day of May, 2005

JON W. DUDAS
*Director of the United States Patent and Trademark Office*